(12) United States Patent
Yamaya

(10) Patent No.: US 8,246,534 B2
(45) Date of Patent: Aug. 21, 2012

(54) ENDOSCOPE

(75) Inventor: Koji Yamaya, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1362 days.

(21) Appl. No.: 11/908,753

(22) PCT Filed: Mar. 30, 2006

(86) PCT No.: PCT/JP2006/306754
§ 371 (c)(1),
(2), (4) Date: Sep. 14, 2007

(87) PCT Pub. No.: WO2006/106881
PCT Pub. Date: Oct. 12, 2006

(65) Prior Publication Data
US 2009/0054727 A1    Feb. 26, 2009

(30) Foreign Application Priority Data
Mar. 31, 2005 (JP) ................. 2005-104340

(51) Int. Cl.
*A61B 1/00* (2006.01)
(52) U.S. Cl. ......... 600/107; 600/104; 600/106; 600/129
(58) Field of Classification Search ........... 600/106–107
See application file for complete search history.

(56) References Cited

U.S. PATENT DOCUMENTS

| | | | | |
|---|---|---|---|---|
| 3,896,793 A | * | 7/1975 | Mitsui et al. | 600/104 |
| 3,897,775 A | * | 8/1975 | Furihata | 600/131 |
| 4,452,236 A | * | 6/1984 | Utsugi | 600/107 |
| 4,949,706 A | * | 8/1990 | Thon | 600/107 |
| 5,343,853 A | * | 9/1994 | Komi | 600/107 |
| 5,562,600 A | * | 10/1996 | Matsuno | 600/107 |
| 6,152,870 A | * | 11/2000 | Diener | 600/107 |
| 2004/0049095 A1 | | 3/2004 | Goto et al. | |
| 2005/0049455 A1 | | 3/2005 | Ootawara et al. | |

FOREIGN PATENT DOCUMENTS

| | | |
|---|---|---|
| DE | 10326579 A1 | 3/2004 |
| JP | 2001-346751 | 12/2001 |
| JP | 2002-34905 | 2/2002 |
| JP | 2002-238836 | 8/2002 |
| JP | 2002-253484 | 9/2002 |
| JP | 2004-57814 | 2/2004 |

OTHER PUBLICATIONS

German Office Action dated Apr. 3, 2012 issued in counterpart German Patent Application No. 11 2006 000 776.9.

* cited by examiner

*Primary Examiner* — Matthew J Kasztejna
(74) *Attorney, Agent, or Firm* — Scully, Scott, Murphy & Presser, P.C.

(57) ABSTRACT

When a guide wire 5 is maximally raised on a treatment instrument raising stand 35, a distal point of the guide wire 5 is operated so as to be capable of always observing a papillary opening portion 7, which is a subject to be treated, from the front (in a basic position where the portion to be treated is positioned at the center of the field of view). The treatment instrument raising stand 35 is maximally raised in order that the tilt angle β of the guide wire 5 is equal to the tilt angle α of a central axis of a field of view of an observation window 30. Then, the guide wire 5 is fixed and a treatment instrument such as a drainage tube is replaced, whereby a treatment instrument can be easily and more safely replaced via the guide wire 5.

6 Claims, 20 Drawing Sheets

ENDOSCOPE

TECHNICAL FIELD

The present invention relates to an endoscope in which a treatment instrument is replaced by using a guide wire in an endoscopic treatment for a pancreaticobiliary duct system, for example.

BACKGROUND ART

Conventionally, a technique has been increasing in which a treatment is performed by frequently replacing various treatment instruments with a guide wire employed as a guide, when a disease in a pancreaticobiliary duct system is endoscopically treated. Therefore, as disclosed in Patent Document 1, for example, an endoscope has been developed in which a guide wire can be fixed to the distal end portion of the insertion unit of the endoscope in order to perform the replacing operation of the treatment instruments in a short period.

An internal diameter of a lumen of a duodenum in a living body is generally about 30 mm. A thickness of a side-view type endoscope for a duodenum is generally set to about 10 mm. Therefore, a maximum of the horizontal distance from a papillary opening portion to an observation window of the endoscope is about 20 mm. On the other hand, the papillary opening portion is anatomically positioned at the lower part (at the side of a small intestine) of the papilla. The advancing direction of a bile duct from the papillary opening portion extends in the upward direction from the papilla (toward a stomach).

Therefore, a viewing direction of an observation optical system in the side-view type endoscope for a duodenum is set so as to be inclined rearward (toward the stomach) at an angle of about 5 to 15 degrees beforehand. The endoscope is designed such that, when the papillary opening portion is observed from the front (at the position at the center of the field of view), the distal end portion of the endoscope is located at the position where the papilla is looked up and the observation and treatment are inevitably done easily. Additionally, when the papillary opening portion is caught at the center of the field of view of the endoscopic image, the endoscopic image of the papillary opening portion that is sharp and bright, and has less distortion can be obtained, compared to the case where the papillary opening portion is caught at the peripheral portion of the screen. Therefore, from the viewpoint of facilitating the replacing operation of the treatment instrument afterwards, it is important for an operator of the endoscope to operate the position of the distal end portion of the endoscope so as to position the distal end portion of the endoscope at the center of the field of view or at the position slightly above the center of the field of view for increasing a sense of looking up the papillary opening portion. In other words, this position is the basic position of the endoscope for a duodenum.

Patent Document 1: Japanese Patent Application Laid-Open No. 2002-34905

DISCLOSURE OF INVENTION

Problem to be Solved by the Invention

According to Patent Document 1, the replacing operation of a treatment instrument is facilitated by a guide wire fixing structure. However, if a distal point of the guide wire, which is apart from the observation window by about 20 mm in the guide wire fixing state (in the state where a treatment instrument raising stand is maximally raised), is not at an appropriate position on the endoscopic image, the operation for slightly drawing or pushing the insertion unit of the endoscope including the distal end portion should be repeated many times. Accordingly, Patent Document 1 entails a problem of troublesome operation, and hence, it takes much time for the entire treatment.

The present invention is accomplished in view of the above-mentioned problem, and its object is to provide an endoscope in which a treatment instrument can simply and more safely be replaced via a guide wire, while always observing a portion to be treated from the front (in a basic position where the portion to be treated is positioned at the center of the field of view).

Means for Solving Problem

An endoscope according to one aspect of the present invention includes an insertion unit that is inserted into a body cavity; an observation optical system that is provided with an observation window formed at a distal end portion of the insertion unit and has a central axis of a field of view in a predetermined direction; a treatment instrument insertion channel that is provided in the insertion unit and is open to the distal end portion of the insertion unit; a treatment instrument raising stand that is capable of guiding a guide wire, which is inserted from a proximal end side of the treatment instrument insertion channel and led out into the body cavity from the distal end portion of the insertion unit, in substantially vertical direction of an endoscopic image taken by the observation optical system; and a guide wire fixing mechanism section that is provided near the distal end portion of the insertion unit. When the guide wire is maximally raised on the treatment instrument raising stand, the guide wire is positioned to have a tilt angle equal to a tilt angle of the central axis of the field of view of the observation window or to have a tilt angle that is smaller than a tilt angle of the central axis of the field of view of the observation window.

An endoscope according to another aspect of the present invention includes an insertion unit that is inserted into a body cavity; an observation optical system that is provided with an observation window formed at a distal end portion of the insertion unit and has a central axis of a field of view in a predetermined direction; a treatment instrument insertion channel that is provided in the insertion unit and is open to the distal end portion of the insertion unit; a treatment instrument raising stand that is capable of guiding a guide wire, which is inserted from a proximal end side of the treatment instrument insertion channel and led out into the body cavity from the distal end portion of the insertion unit, in substantially vertical direction of an endoscopic image taken by the observation optical system; and a guide wire fixing mechanism section that is provided near the distal end portion of the insertion unit. When the guide wire is maximally raised on the treatment instrument raising stand, a distal point of the guide wire apart from the observation window by about 20 mm is positioned near a central line, which divides a screen of the endoscopic image equally in the vertical direction, or positioned at an area above the central line.

In the endoscope according to the invention, a point at which an extension line and a plane apart from the observation window by about 20 mm are intersected may be positioned closer to a proximal end side from a position at which the central axis of the field of view of the observation window and the plane cross each other, the extension line being obtained by extending a perpendicular that links a contact portion at which the treatment instrument raising stand and the guide wire are brought into contact with each other and a support shaft of the treatment instrument raising stand.

An endoscope according to still another aspect of the present invention includes an insertion unit that is inserted into a body cavity; an observation optical system that is provided with an observation window formed at a distal end portion of the insertion unit and has a central axis of a field of view in a predetermined direction; a treatment instrument insertion channel that is provided in the insertion unit and is open to the distal end portion of the insertion unit; a treatment instrument raising stand that is capable of guiding a guide wire, which is inserted from a proximal end side of the treatment instrument insertion channel and led out into the body cavity from the distal end portion of the insertion unit, in substantially vertical direction of an endoscopic image taken by the observation optical system; and a guide wire fixing mechanism section that is provided near the distal end portion of the insertion unit. When the guide wire is maximally raised on the treatment instrument raising stand, a relationship between a tilt angle $\alpha$ of the central axis of the field of view of the observation window, a tilt angle $\beta$ of the guide wire, and an angle of view 7 above the center of the field of view satisfies 20 tan $\alpha \leq L$+20 tan $\beta$<20 tan($\alpha$+$\gamma$), wherein L is a horizontal distance in an axial direction between a proximal end portion of the guide wire which is maximally raised and the center of the field of view on the observation window.

An endoscope according to still another aspect of the present invention of includes an insertion unit that is inserted into a body cavity; a distal end portion that is formed at a distal end portion of the insertion unit; an observation optical system that is provided at the distal end portion, and has a central axis of a field of view directing toward the direction tilted with respect to the distal end portion with a predetermined angle so as to pick up an image of an inside of the body cavity in a direction of the field of view as an observation image; a treatment instrument insertion channel that is provided in the insertion unit and has a channel into which the guide wire is inserted; an opening portion that is communicated with the treatment instrument insertion channel and is open to a main body of the distal end portion; a treatment instrument raising stand that is provided with a guide portion for guiding the guide wire protruding from the opening portion, and that is capable of guiding a distal end of the guide wire to a position that exceeds a predetermined angular range made by the central axis of the field of view and the distal end portion, when the guide wire protrudes from the opening portion by a predetermined distance; and a guide wire fixing mechanism section that fixes the guide wire, which is guided to the position by the treatment instrument raising stand, to the opening portion.

An endoscope according to still another aspect of the present invention includes an insertion unit that is inserted into a body cavity; a distal end portion formed at a distal end of the insertion unit; an observation optical system that is provided at the distal end portion, and has a central axis of a field of view directing toward a direction tilted a predetermined angle with respect to the distal end portion so as to pick up an image of an inside of the body cavity in the direction of the field of view as an observation image; a treatment instrument insertion channel that is provided in the insertion unit and has a channel into which the guide wire is inserted; an opening portion that is communicated with the treatment instrument insertion channel and is open to a main body of the distal end portion; a treatment instrument raising stand that is provided with a guide portion for guiding the guide wire protruding from the opening portion, and that is capable of guiding a distal end of the guide wire to a position that exceeds a predetermined angular range made by the central axis of the field of view and the distal end portion, when the guide wire protrudes from the opening portion to a position apart from the observation window by a predetermined distance; and a guide wire fixing mechanism section that fixes the guide wire, which is guided to the position by the treatment instrument raising stand, to the opening portion.

An endoscope according to still another aspect of the present invention includes an insertion unit that is inserted into a body cavity; a distal end portion formed at a distal end of the insertion unit; an observation optical system that is provided at the distal end portion, and has a central axis of a field of view directing toward a direction tilted a predetermined angle with respect to the distal end portion so as to pick up an image of an inside of the body cavity in the direction of the field of view as an observation image; a treatment instrument insertion channel that is provided in the insertion unit and has a channel into which the guide wire is inserted; an opening portion that is communicated with the treatment instrument insertion channel and is open to a main body of the distal end portion; a treatment instrument raising stand that is provided with a guide portion for guiding the guide wire protruding from the opening portion, and that is capable of guiding a distal end of the guide wire so as to have an angle larger than that made by the central axis of the field of view and the distal end portion, when the guide wire protrudes from the opening portion by a predetermined distance; and a guide wire fixing mechanism section that fixes the guide wire, which is guided by the treatment instrument raising stand so as to have an angle greater than the angle made by the central axis of the field of view and the distal end portion, to the opening portion.

EFFECT OF THE INVENTION

In an endoscope according to the present invention, when a guide wire inserted into a body cavity from a distal end portion of an insertion unit is maximally raised on a treatment instrument raising stand, the guide wire is positioned in such a manner that a tilted angle of the guide wire is equal to a tilt angle of a central axis of the field of view of an observation window or the tilted angle of the guide wire is smaller than the tilt angle of the central axis of the field of view of the observation window. Accordingly, the endoscope of the present invention provides an effect that a treatment instrument can simply and more safely be replaced via the guide wire while always observing a portion to be treated from the front (in a basic position where the portion to be treated is positioned at the center of the field of view).

EXPLANATIONS OF LETTERS OR NUMERALS

Figure 1:
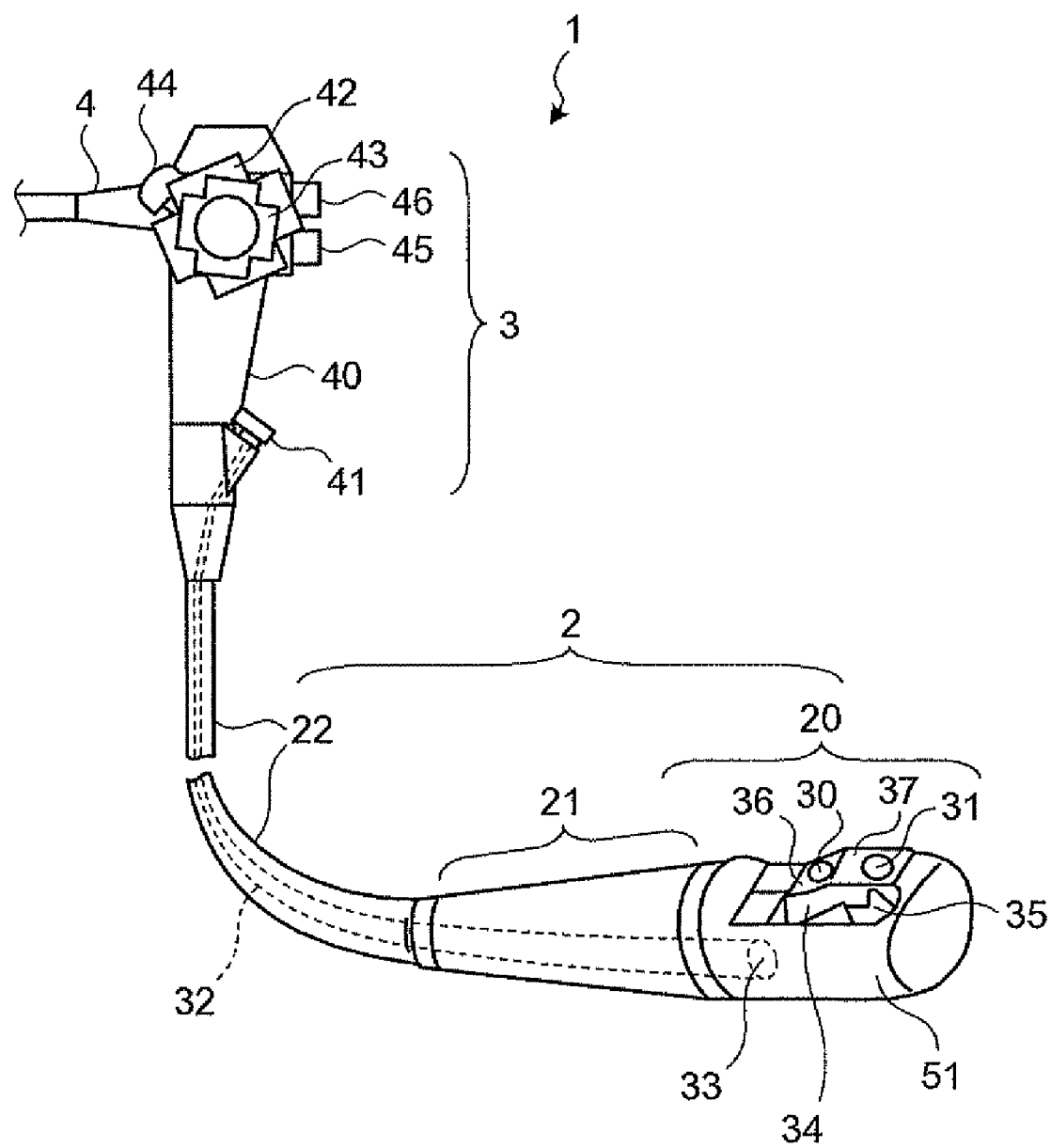
FIG. 1 is a structural view showing an overall structure of an endoscope according to the present invention.

1 Endoscope
2 Insertion unit
3 Operation unit
4 Universal cord
5 Guide wire
5a Guide wire small-diameter portion
5b Guide wire large-diameter portion
6 Duodenum
7 Papillary opening portion
8 Papilla
9 Bile duct
20 Distal end portion
21 Bendable portion
22 Soft portion
30 Observation window
31 Illumination window
32 Treatment instrument insertion channel
33 Treatment instrument lead-out port
34 Treatment instrument lead-out portion
35 Treatment instrument raising stand
35a Guide channel
35b Guide wire housing channel
36 Inclined surface
37 Horizontal surface
38 Support shaft
40 Grip portion
41 Treatment instrument insertion port
42, 43 Bending operation knobs
44 Raising lever
45 Air-supply/water-supply button
46 Suction operation button
50 Distal end portion composing unit
51 Distal end cover
52 Joint member
52a Taper
53 Insulating block
54 Operation wire
55 Terminal member
56 Stopper
57 Terminal reinforcing member
58 Operation wire fixing hole
59 Contrast tube
60 Adhesive
61 Channel internal diameter decreasing portion
62 Light guide fiber
63 Imaging unit
64 Nozzle
C Proximal end portion
E, G Illumination range
F Observation range
M Plane
Q, R Center line
S Central axis of field of view
Y Distal point

BEST MODE(S) FOR CARRYING OUT THE INVENTION

Embodiments of an endoscope according to the present invention will be explained in detail with reference to FIGS.

1 to 30. The present invention is not limited to these embodiments, and various modified embodiments are possible without departing from the scope of the present invention.

First Embodiment

FIG. 1 is a block diagram showing an overall structure of the endoscope according to the present invention. In the figure, the endoscope 1 has an elongated cylindrical insertion unit 2 that is inserted into a subject to be treated, and an operation unit 3 joined to the base portion of the insertion unit 2. A flexible extended universal cord 4 for detachably connecting a light source device or image processing device, not shown, to the operation unit 3 is provided to the side part of the operation unit 3.

The insertion unit 2 has a rigid distal end portion 20, and a bendable portion 21 which is bendable and a soft portion 22, which are formed at the rear end of the distal end portion 20. The soft portion 22 is long and has a flexibility. The soft portion 22 is joined to the rear end of the bendable portion 21.

An observation window 30 serving as an observation optical system and an illumination window 31 serving as an illumination optical system are provided at the side part of the distal end portion 20 so as to be capable of being viewed from the side. A treatment instrument lead-out portion 34 serving as an opening provided with a treatment instrument lead-out port 33 of a treatment instrument insertion channel 32 is provided at the distal end portion 20 together with the observation window 30 and the illumination window 31. A treatment instrument raising stand 35 is pivotably provided in the treatment instrument lead-out portion 34 in the vicinity of the treatment instrument lead-out port 33.

A grip portion 40 is provided at the operation unit 3. The grip portion 40 is provided with a treatment instrument insertion port 41 at its distal end portion. The treatment instrument insertion port 41 is communicated with the above-mentioned treatment instrument insertion channel 32. A treatment instrument not illustrated is inserted from the treatment instrument insertion port 41, passes through the treatment instrument insertion channel 32, and is projected from the treatment instrument lead-out port 33. The treatment instrument is guided in a predetermined direction through the treatment instrument raising stand 35 that can be raised and lowered by a remote control.

Two bending operation knobs 42 and 43 and a raising lever 44 are mounted to the operation unit 3. The bending operation knobs 42 and 43 are knobs for bending the bendable portion 21 in the vertical direction and side-to-side direction with a remote control. The raising lever 44 is a knob for operating the treatment instrument raising stand 35 in the vertical direction through a remote control. Provided to the operation unit 3 are an air-supply/water-supply operation button 45, suction operation button 46, and the like.

Figure 2:
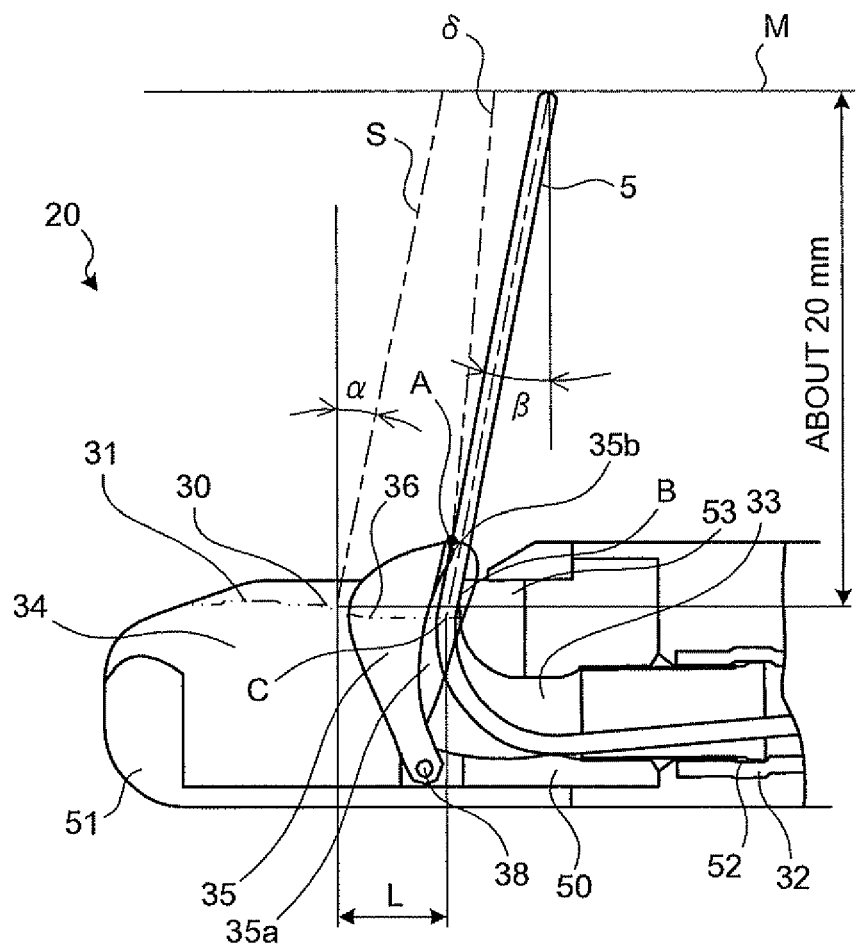
FIG. 2 is a view showing a partial section of a distal end portion shown in FIG. 1 when a guide wire according to a first embodiment is brought into its fixed state by a treatment instrument raising stand maximally raising.
Figure 3:
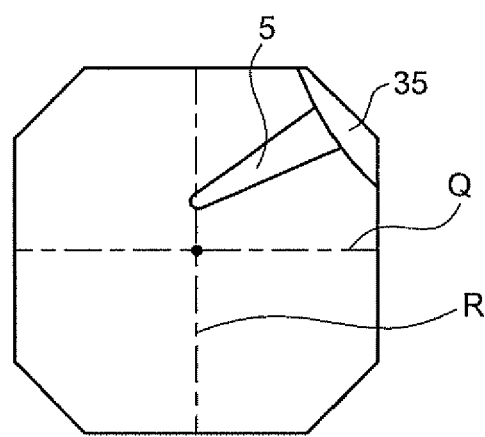
FIG. 3 is a view showing an endoscopic image with the state shown in FIG. 2.

FIG. 2 is a view showing a part of the section of the distal end portion shown in FIG. 1 when a guide wire is brought into its fixed state by maximally raising the treatment instrument raising stand. FIG. 2 shows the actual position of the distal end portion of the guide wire 5 when the guide wire 5 projecting from the distal end portion 20 of the endoscope 1 is fixed by the maximum raise of the treatment instrument raising stand 35 at the position apart from the observation window 30 by about 20 mm. FIG. 3 is a view showing an image of the endoscope with the state shown in FIG. 2. The observation window 30 and the illumination window 31 are illustrated by a two-dot-chain line from the viewpoint of being projected at the side of the treatment instrument lead-out port portion 34. The observation window 30 is formed at an inclined surface 36, and the illumination window 31 is formed on a horizontal surface 37 of the inclined surface 36 at its distal end.

In general, an internal diameter of a lumen of a duodenum is known as about 20 to 30 mm. A diameter of an endoscope generally used for an alimentary canal is approximately 10 mm. When the endoscope described above is inserted into the lumen, the clearance between the wall of the lumen and the endoscope increases to a maximum of about 20 mm. The clearance depends upon the outer diameter of the treatment instrument, or flexibility or spring-back property of a flexible tube composing the insertion unit. If a flexible tube has a bending tendency, the distance between the treatment instrument and the section to be treated may be different, and the treatment instrument and the section to be treated may be close to each other.

When the outer diameter of the endoscope is small, the clearance may increase by that much. Specifically, considering the above-mentioned case, the treatment may be performed with the clearance of about 10 to 20 mm defined as a section to be treated. Specifically, in case where the extension line δ which is obtained by extending the perpendicular that links the contact portion where the treatment instrument raising stand 35 and the guide wire 5 are brought into contact with each other and the support shaft 38 of the treatment instrument raising stand 35 crosses the plane M, which is apart from the observation window 30 by the above-mentioned distance, at the position close to the base side from the position where the central axis S of the field of view crosses the plane M, the treatment property is enhanced.

The treatment instrument raising stand 35 is configured such that the proximal end portion thereof is held by a support shaft 38 so as to be capable of pivoting, whereby the treatment instrument raising stand 35 can be operated in the substantially vertical direction from the base portion of the operation unit 3 through a remote control by an operation wire not illustrated. A guide channel 35*a*, serving as a guide portion for guiding the treatment instrument, is formed in the treatment instrument raising stand 35 all over the length thereof. A narrow guide wire housing channel 35*b* having an outer diameter of about 0.035 inch for storing the guide wire 5 is formed at the distal end portion of the guide channel 35*a*. It is to be noted that the sectional shape of the guide wire housing channel 35*b* is not limited, and it may be V-shaped or U-shaped.

The distal end portion 20 is composed of a distal end portion composing unit 50 made mainly of a metallic body and a distal end cover 51 made of resin or rubber formed from an electrical insulating material. The treatment instrument insertion channel 32 is joined to the rear end of the distal end portion composing unit 50 through a joint member 52. An insulating block 53, made of an electrical insulating material such as ceramic, is provided at the vicinity of the treatment instrument lead-out port 33 so as to form a part of the treatment instrument lead-out port 33. It is to be noted that the insulating block 53 may not be formed, and the treatment instrument lead-out port 33 may be composed only of the distal end portion composing unit 50.

When the treatment instrument raising stand 35 is maximally raised, the guide wire 5 is held at two points, which are an A point where the guide wire housing channel 35*b* is in the strongest contact and a point B where the insulating block 53 at the side of the treatment instrument lead-out port 33 is brought into contact, whereby the guide wire 5 can firmly be fixed. The guide wire housing channel 35*b* and the insulating block 53 compose a guide wire fixing mechanism section according to the present invention. When the insulating block 53 is not provided, the guide wire housing channel 35b and the distal end portion composing unit 50 compose the guide wire fixing mechanism section. The reason why the guide wire 5 is fixed at two points that are apart from each other across the guide wire 5 is because this structure provides less damage to the guide wire 5, compared to the case in which the guide wire is nipped at one point of generally the same position. When the guide wire 5 is maximally raised on the treatment instrument raising stand 35 and held and fixed at two points, the tilt angle of the guide wire 5 becomes an angle β. The tilt angle of a central axis S of the field of view of the observation window 30 is an angle α. The horizontal distance between the proximal end portion C of the guide wire 5, which is maximally raised, and the central axis S of the field of view above the observation window 30 in the axial direction is a distance L. The proximal end portion C of the guide wire 5 indicates the portion of C that is most projected toward the distal end portion of the distal end portion 20 when the guide wire 5 is maximally raised on the treatment instrument raising stand 35 to be fixed as shown in FIG. 2.

This embodiment provides a configuration in which the treatment instrument raising stand 35 can be maximally raised in order that the tilt angle β of the guide wire 5 is equal (β=α) to the tilt angle α of the central axis S of the field of view of the observation window 30. Further, this embodiment provides a configuration in which the treatment instrument raising stand 35 can be maximally raised in order that the tilt angle β of the guide wire 5 is smaller (β<α) than the tilt angle α of the central axis S of the field of view of the observation window 30. The maximum raise of the treatment instrument raising stand 35 can be realized by pivoting the treatment instrument raising stand 35 about the support shaft 38 through a remote control from the base portion of the operation unit 3 by the operation wire as described above. In FIG. 2, the tilt angle β of the guide wire 5 is set to be equal to the tilt angle α of the central axis S of the field of view of the observation window 30.

In FIG. 2, the plane including the central axis S of the field of view extending from the observation window 30 and perpendicular to the figure corresponds to the center line Q that divides the image of the endoscope of the observation system shown in FIG. 3 equally in the vertical direction, wherein the upper part corresponds to the base of the distal end portion 20 and the lower part corresponds to the distal end portion of the distal end portion 20. On the other hand, the center line R is a line dividing the image of the endoscope equally in the side-to-side direction.

Figure 4:
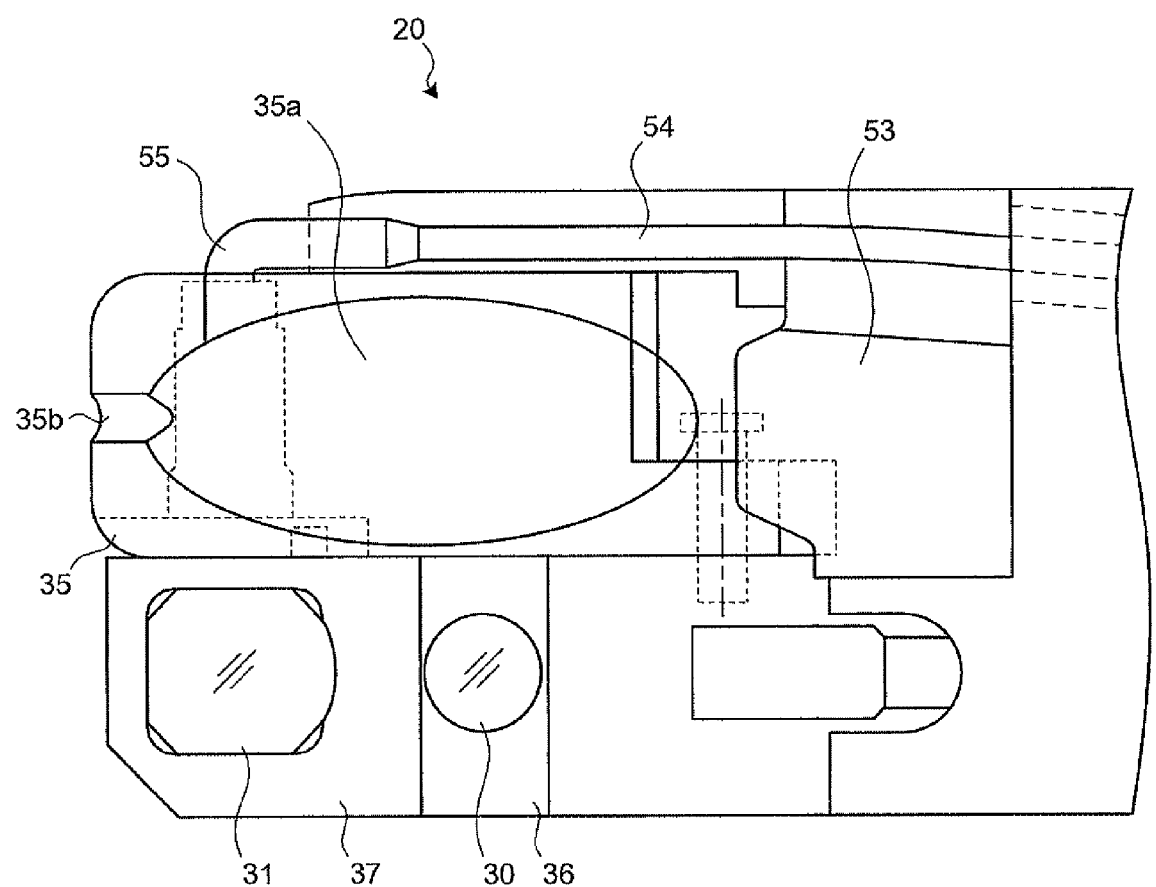
FIG. 4 is a top view partially showing a top surface of the distal end portion shown in FIG. 1.
Figure 5:
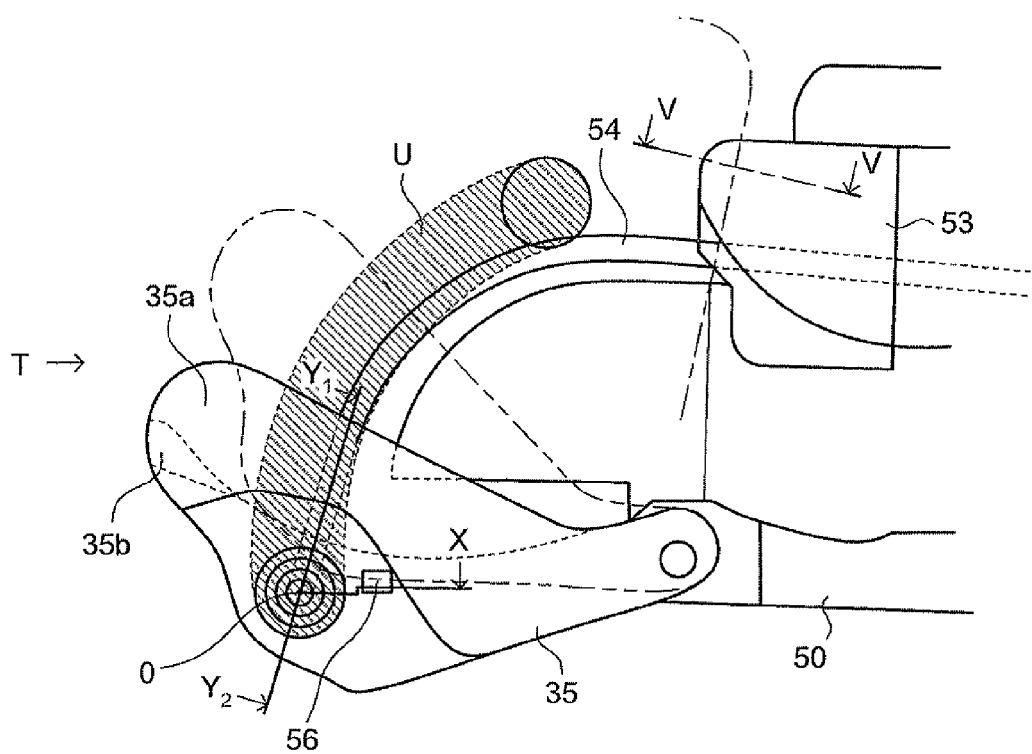
FIG. 5 is a side view partially showing a side surface of the distal end portion shown in FIG. 4 from which a distal end cover is removed.
Figure 6:
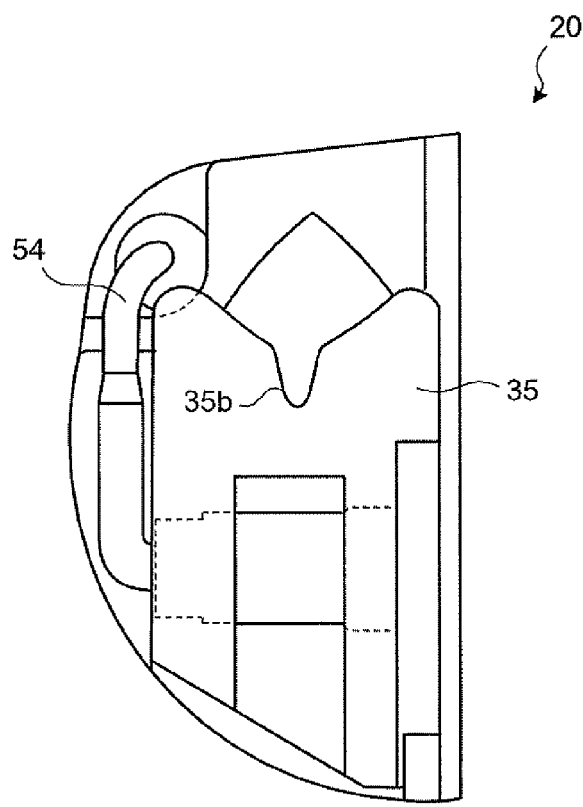
FIG. 6 is a fragmentary view taken in the direction of arrow T in FIG. 5.
Figure 7:
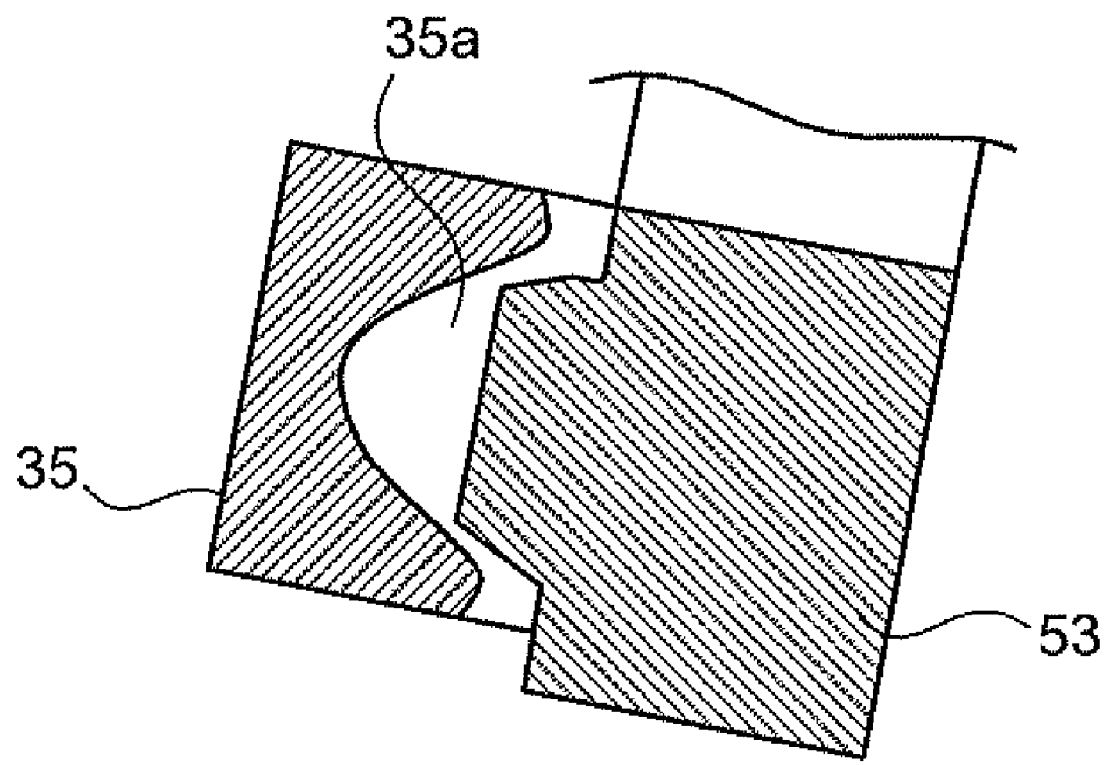
FIG. 7 is a sectional view showing the V-V section in FIG. 5.
Figure 8:
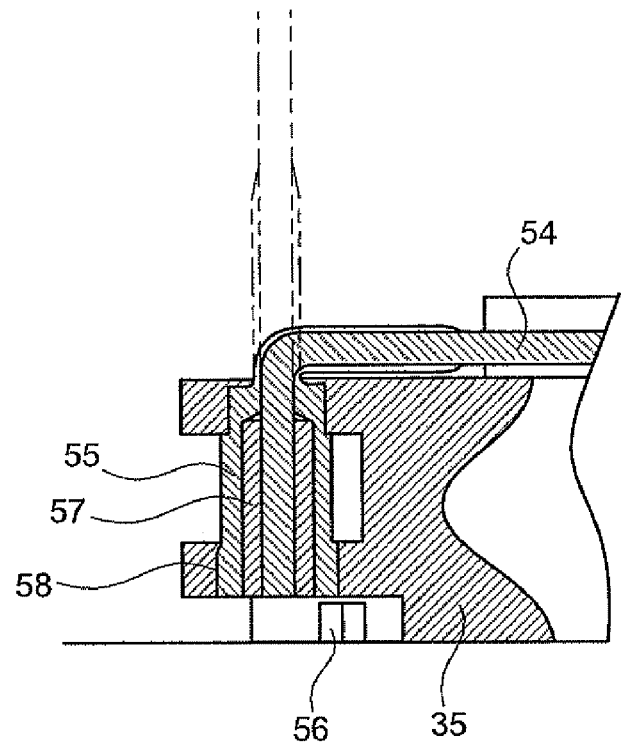
FIG. 8 is a sectional view showing the Y1-Y2 section in FIG. 5.
Figure 9:
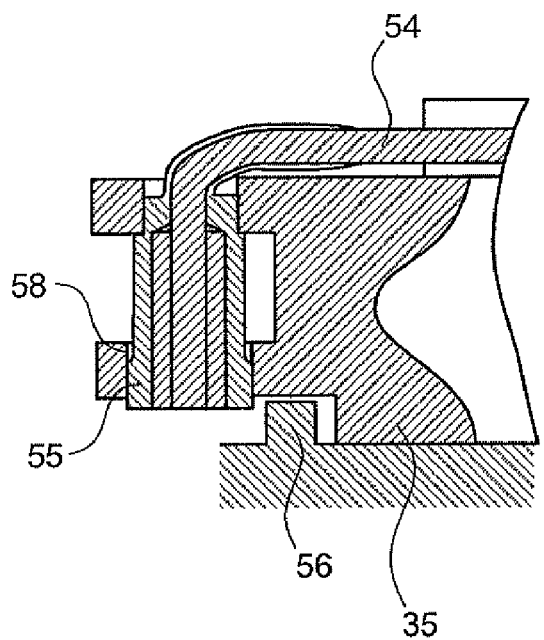
FIG. 9 is a sectional view showing the Y1-O-X section in FIG. 5.

FIG. 4 is a top view showing a part of the distal end portion shown in FIG. 1. FIG. 5 is a side view showing a part of the side face of the distal end portion shown in FIG. 4 from which the distal end cover is removed. FIG. 6 is a fragmentary view taken in the direction of an arrow T in FIG. 5. FIG. 7 is a sectional view taken along line V-V in FIG. 5. FIG. 8 is a sectional view taken along line Y1-Y2 in FIG. 5. FIG. 9 is a sectional view taken along line Y1-O-X in FIG. 5.

In these figures, an operation wire 54 is joined to the treatment instrument raising stand 35 via a terminal member 55. The distal end of the operation wire 54 penetrates the terminal member 55 to be held. The operation wire 54 is pushed toward the distal end of the operation wire 54 and pulled toward the base thereof, whereby the treatment instrument raising stand can be raised or lowered. As shown in FIG. 5, a stopper 56 is provided at the side where the treatment instrument raising stand 35 is lowered. This stopper 55 is projected integrally from the distal end portion composing unit 50. Further, this stopper 56 is positioned at the inside (base side) of the projecting area U where the terminal member 55 of the operation wire 54 moves.

The guide channel 35a is formed into a concave shape whose plane is elliptic as shown in FIGS. 4 and 6. The guide wire housing channel 35b having a concave shape is formed at the distal end portion of the guide channel 35a. As shown in FIG. 7, when the treatment instrument raising stand 35 is maximally raised with the movement of the operation wire 54 toward the proximal end side, a part of the insulating block 53 is fitted into the guide channel 35a of the treatment instrument raising stand 35 so as not to be in contact with the guide channel 35a. Specifically, the treatment instrument raising stand 35 is configured to be capable of being maximally elevated in a limited space.

A terminal reinforcing member 57 is fixed at the tip of the operation wire 54 as shown in FIGS. 8 and 9. The terminal member 55 is fixed at the outside of the terminal reinforcing member 57. The terminal member 55 is rotatably held in such a manner that the terminal member 55 is inserted into an operation wire fixing hole 58 formed on the treatment instrument raising stand 35 with the state indicated by a two-dot-chain line (see FIG. 8), and then, one end of the terminal member 55 is bent at an angle of about 90° with the operation wire 54. Since the repeated bending force is applied to the terminal member 55, the terminal member 55 is slightly projected from the operation wire fixing hole 58 as shown in FIG. 9. However, since the stopper 56 shown in FIG. 5 is positioned at the inside of the projecting area U where the terminal member 55 of the operation wire 54 moves, there is no chance that the stopper 56 and the terminal member 55 are brought into contact with each other. Accordingly, this embodiment is configured to prevent the poor lowering of the treatment instrument raising stand 35 caused by years of use.

Figure 10:
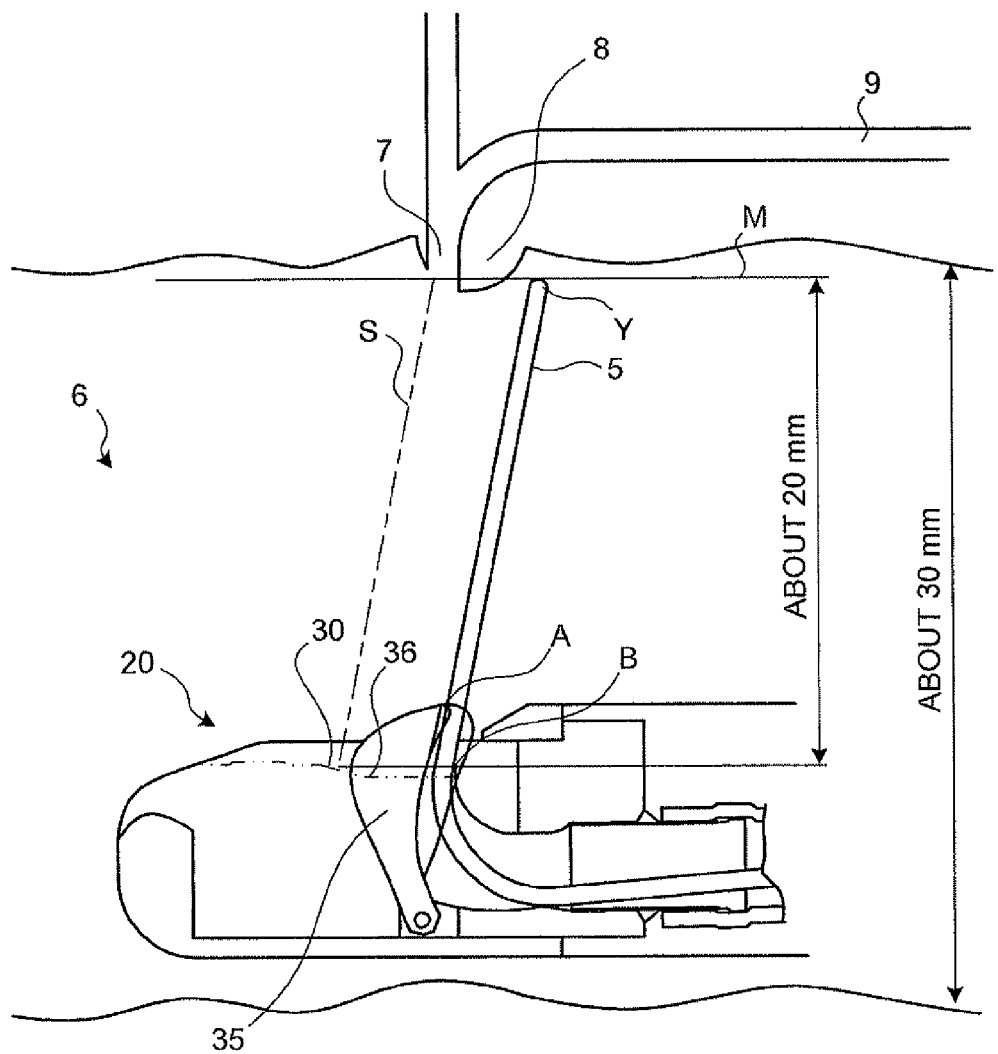
FIG. 10 is a view partially showing a section of the distal end portion shown in FIG. 1 for explaining an operation of the guide wire before being inserted into a bile duct.
Figure 11:
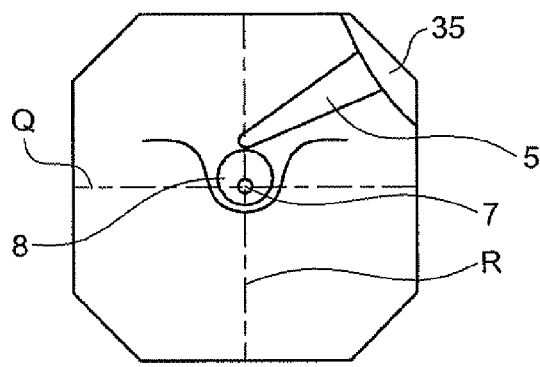
FIG. 11 is a view showing an endoscopic image with the state shown in FIG. 10.

Subsequently, a series of operations from the insertion of the guide wire 5 into a bile duct 9 to the replacement of the treatment instrument by using the endoscope 1 according to the present embodiment will be explained with reference to FIGS. 10 to 15. As shown in FIGS. 10 and 11, the position of the distal end (distal point Y) of the fixed guide wire 5 reaches the proximal end side (at the upper side in FIG. 10) from the central axis S of the field of view at a distance of about 20 mm apart from the observation window 30 of the distal end portion 20 of the endoscope 1 inserted into the duodenum 6. After the papillary opening portion 7 and the neighboring papilla 8 are well observed at the basic position of the central axis S of the field of view where the papillary opening portion 7 is caught, the subsequent operation can be performed with the basic position always kept.

Figure 12:
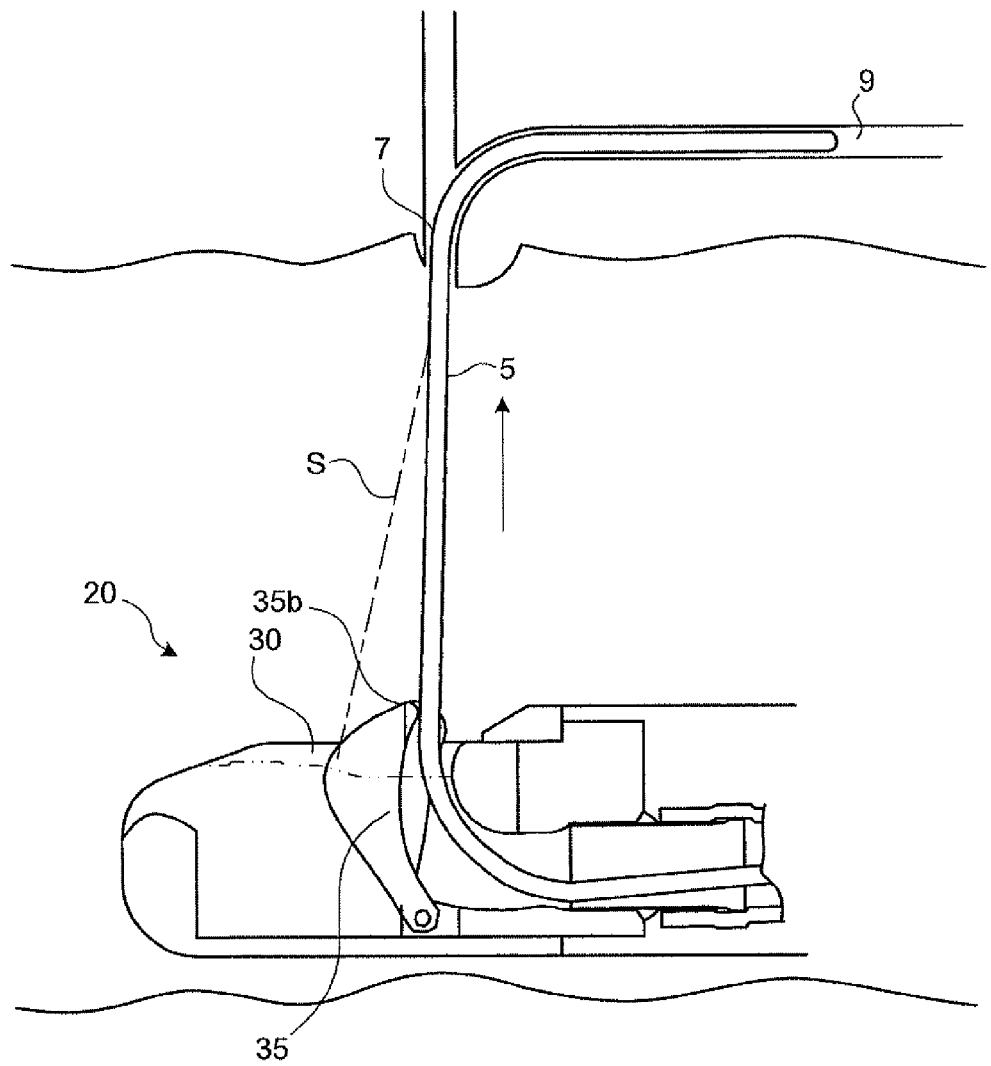
FIG. 12 is a view partially showing a section of the distal end portion shown in FIG. 1 for explaining an operation of the guide wire during the insertion into a bile duct.
Figure 13:
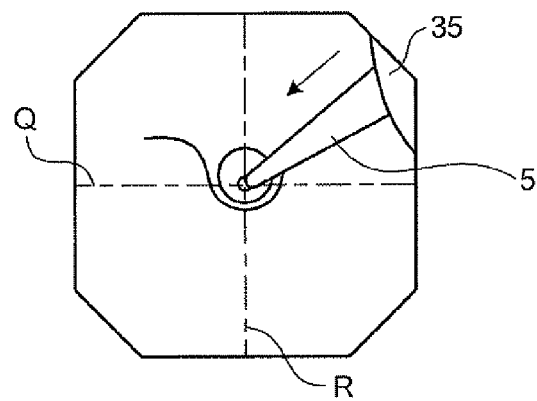
FIG. 13 is a view showing an endoscopic image with the state shown in FIG. 12.

Specifically, as shown in FIGS. 12 and 13, the treatment instrument raising stand 35 is slightly lowered with the basic position maintained at the next operation. With this operation, the distal end of the guide wire 5 is changed to the position of the papillary opening portion 7, and then, the guide wire 5 is inserted into the bile duct 9 from the papillary opening portion 7.

Figure 14:
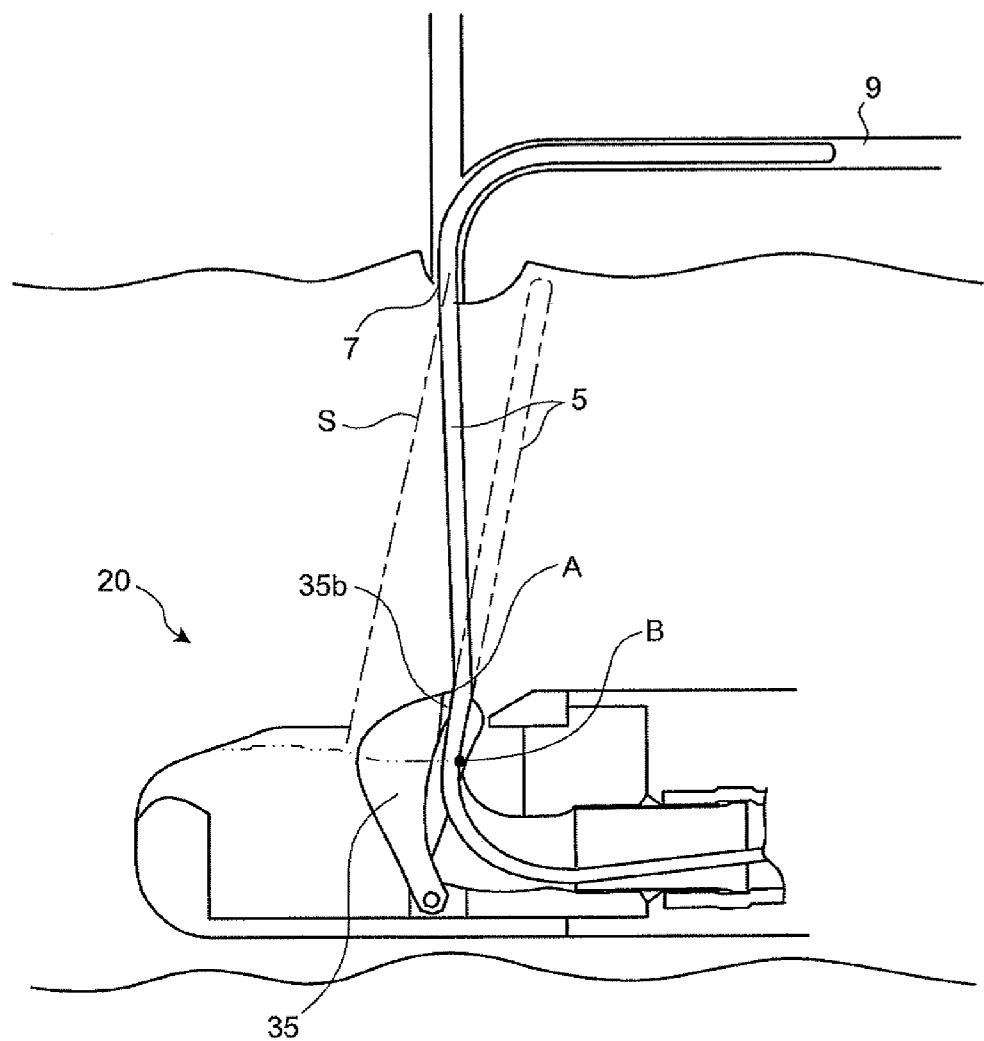
FIG. 14 is a view partially showing a section of the distal end portion shown in FIG. 1 for explaining an operation of the guide wire after being inserted into a bile duct.
Figure 15:
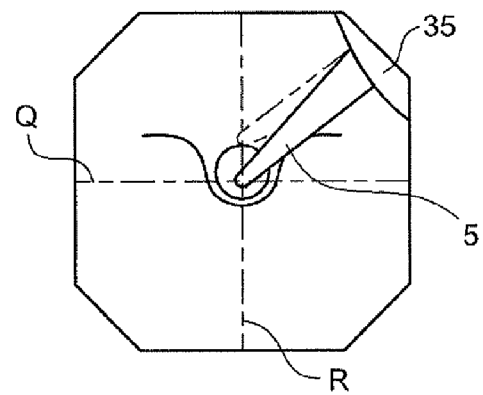
FIG. 15 a view showing an endoscopic image with the state shown in FIG. 14.

Next, as shown in FIGS. 14 and 15, the guide wire 5 is inserted into the bile duct 9 to an appropriate depth. Thereafter, the treatment instrument raising stand 35 is maximally raised to fix the guide wire 5. With this operation, the guide wire 5 can also easily be fixed with the basic position maintained. The projecting direction in which the guide wire 5 can be fixed with the guide wire 5 not inserted into the papillary opening portion 7 is the direction indicated by a two-dot-chain line like FIG. 10. Specifically, the direction indicated by a solid line is the direction in which the guide wire 5 is more firmly held by the guide wire housing channel 35b compared to the state indicated by a two-dot-chain line. Therefore, even when a treatment instrument such as a drainage tube is pushed from the proximal end side of the guide wire 5 through the guide wire 5, there is no chance that the distal end of the guide wire 5 advances to the far side of the bile duct 9 together with the treatment instrument.

As described above, according to the present embodiment, the guide wire 5 can be maximally raised on the treatment instrument raising stand 35 in order that the tilt angle β of the guide wire 5 is equal to the tilt angle α of the central axis S of the field of view of the observation window 30. By virtue of this configuration, a treatment instrument can easily and more safely be replaced through the guide wire, while always observing the papillary opening portion 7 as a portion to be treated from the front (in a basic position where the portion to be treated is positioned at the center of the field of view), according to the present embodiment. Further, in the present invention, when the guide wire 5 is maximally raised on the treatment instrument raising stand 35 in such a manner that β<α is established, a treatment instrument can easily and more safely be replaced through the guide wire, while always observing the papillary opening portion as a portion to be treated from the front (in a basic position where the portion to be treated is positioned at the center of the field of view). Specifically, the present embodiment provides enhanced cannulation property of a treatment instrument.

Meanwhile, the first embodiment is characterized in that, when the guide wire 5 is maximally raised on the treatment instrument raising stand 35, the guide wire 5 is positioned such that the tilt angle β of the guide wire 5 is equal to the tilt angle α of the central axis S of the field of view of the observation window 30, or the tile angle β is smaller than the tilt angle α (β<α). When this characteristic is shown in the image of the endoscope shown in FIG. 3, the distal point of the guide wire 5 apart from the observation window 30 by about 20 mm is positioned in the vicinity of the center line Q, which divides the screen of the image of the endoscope equally in the vertical direction, or in the area above the center line Q (at the proximal end side of the distal end portion 20), when the guide wire 5 is maximally raised on the treatment instrument raising stand 35.

If the field angle of the upper half screen of the image of the endoscope is made narrower than the field angle of the lower half, the magnification ratio at the upper side of the field of view can be increased more than the that at the lower side of the field of view. Accordingly, a papilla can be easily seen when caught at the upper side of the field of view.

Figure 16:
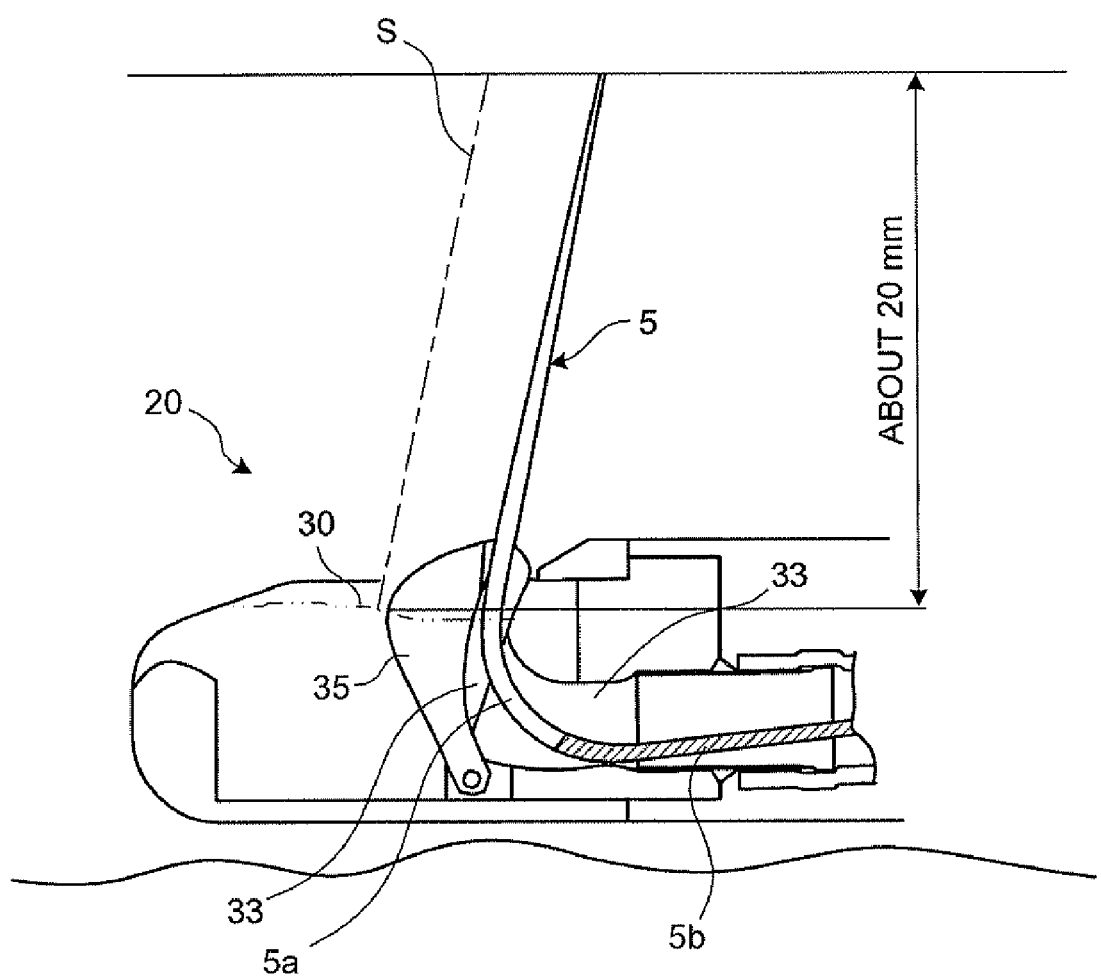
FIG. 16 is a view partially showing a section of the distal end portion shown in FIG. 1 when a small-diameter portion of the guide wire according to a first modification of the first embodiment is positioned in the vicinity of a treatment instrument lead-out port.

In the first embodiment, it is described that the guide wire 5 is fixed in FIGS. 2 and 10. However, the present invention is not limited thereto. For example, the guide wire 5 may be in its non-fixed state as shown in FIG. 16 according to a first modification. If the fixed state shown in FIG. 17 described later is produced, the operation and effect same as those in the first embodiment are obtained. The modification will be explained below.

The guide wire 5 according to the modification is partly different in shape from the guide wire 5 shown in FIG. 2 or FIG. 10. Specifically, in the modification, a guide wire small-diameter portion 5a is formed at the distal end portion of the guide wire 5 in order to enhance insertion property to the papillary opening portion 7. The small-diameter portion 5a is tapered toward the distal end portion.

FIG. 16 shows a state in which the guide wire small-diameter portion 5a is positioned in the vicinity of the treatment instrument lead-out port 33. In this state, the position of the distal end portion of the guide wire 5 apart from the observation window 30 by about 20 mm reaches the tilt angle of the central axis S of the field of view, like FIG. 2 or FIG. 10, even when the guide wire 5 is maximally raised on the treatment instrument raising stand 35. However, since the proximal end of the guide wire 5 is smaller than that in the case of FIG. 2 or FIG. 10, the guide wire 5 cannot be fixed. When the guide wire 5 is further led out to position a guide wire large-diameter portion 5b of the guide wire 5 in the vicinity of the treatment instrument lead-out port 33, the guide wire 5 can be fixed as shown in FIG. 17.

Figure 17:
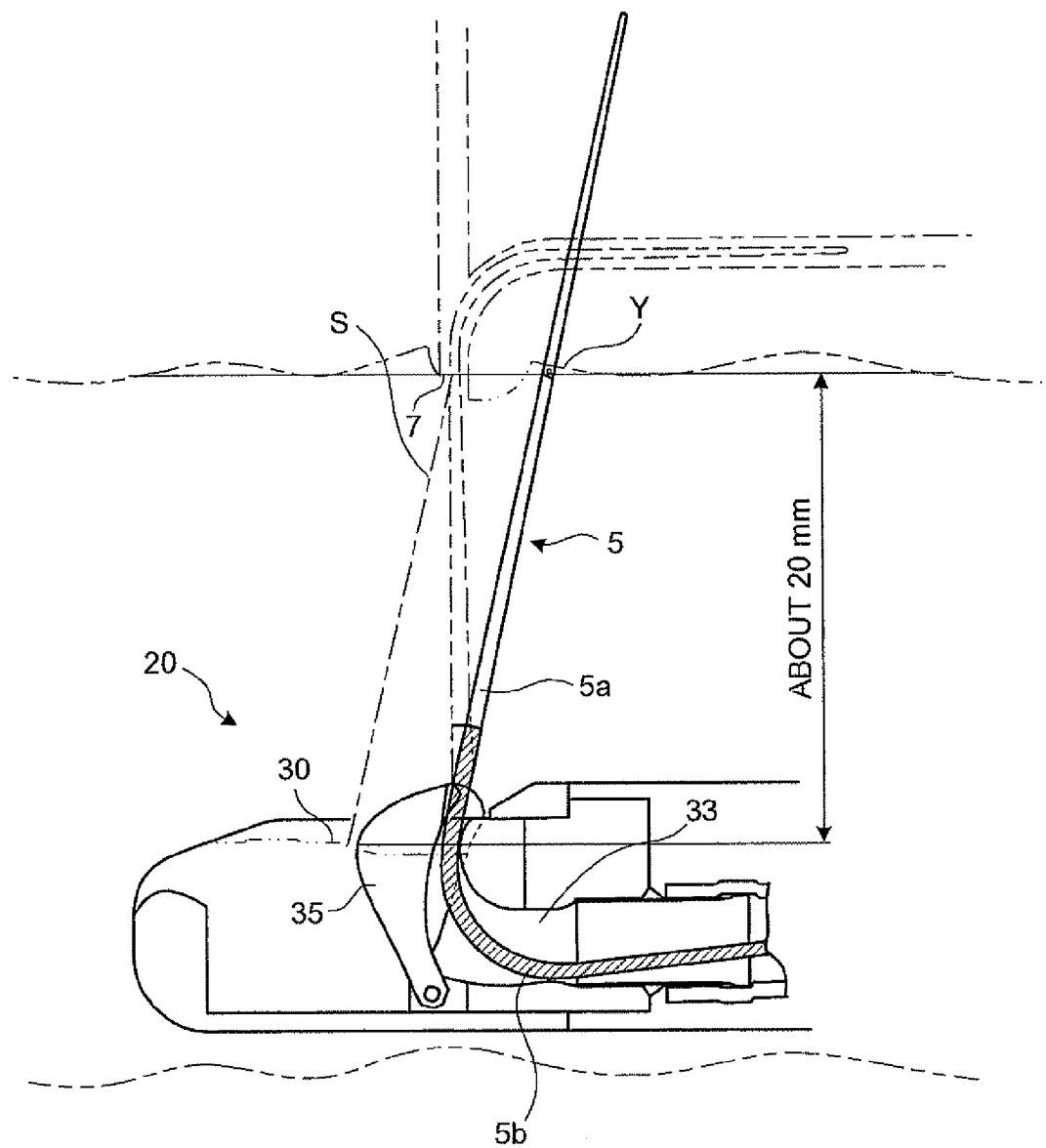
FIG. 17 is a view partially showing the section of the distal end portion shown in FIG. 1 when a large-diameter portion of the guide wire according to the first modification of the first embodiment is maximally raised.

FIG. 17 is a view showing that the guide wire large-diameter portion 5b at the proximal end side of the guide wire 5 is maximally raised. In this figure, the distal point Y of the guide wire 5 apart from the observation window 30 by about 20 mm reaches the tilt angle of the central axis S of the field of view, and further the fixation is achieved. The two-dot-chain line indicates that the guide wire large-diameter portion 5b is maximally raised to fix the guide wire 5 after the guide wire 5 is inserted into the papillary opening portion 7 at the basic position. This modification provides the operation and effect same as those in the first embodiment.

Specifically, in the first embodiment and the first modification, the distal point Y of the guide wire 5 apart from the observation window 30 by about 20 mm in the fixed state (when the treatment instrument raising stand is maximally raised) is located at the optimum position on the image of the endoscope. Therefore, according to the first embodiment and the first modification, a series of operations from the insertion of the guide wire 5 to the replacement of the treatment instrument can easily and smoothly be performed at the basic position at any time, with the result that the whole treatment time can significantly be shortened.

Figure 18:
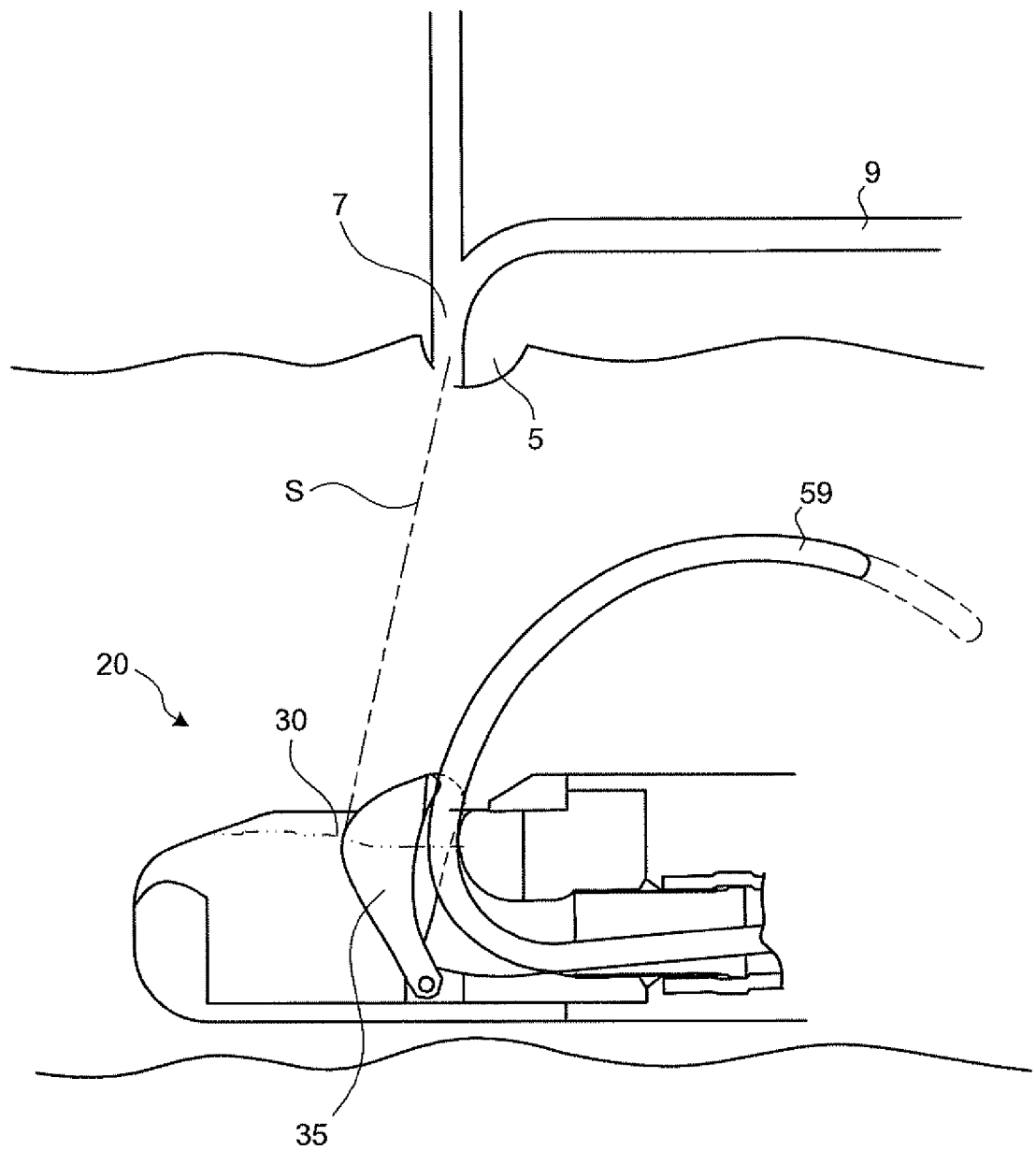
FIG. 18 is a view partially showing a section of the distal end portion shown in FIG. 1 when a contrast tube according to a second modification of the first embodiment is brought into its fixed state by a treatment instrument raising stand maximally raising.
Figure 19:
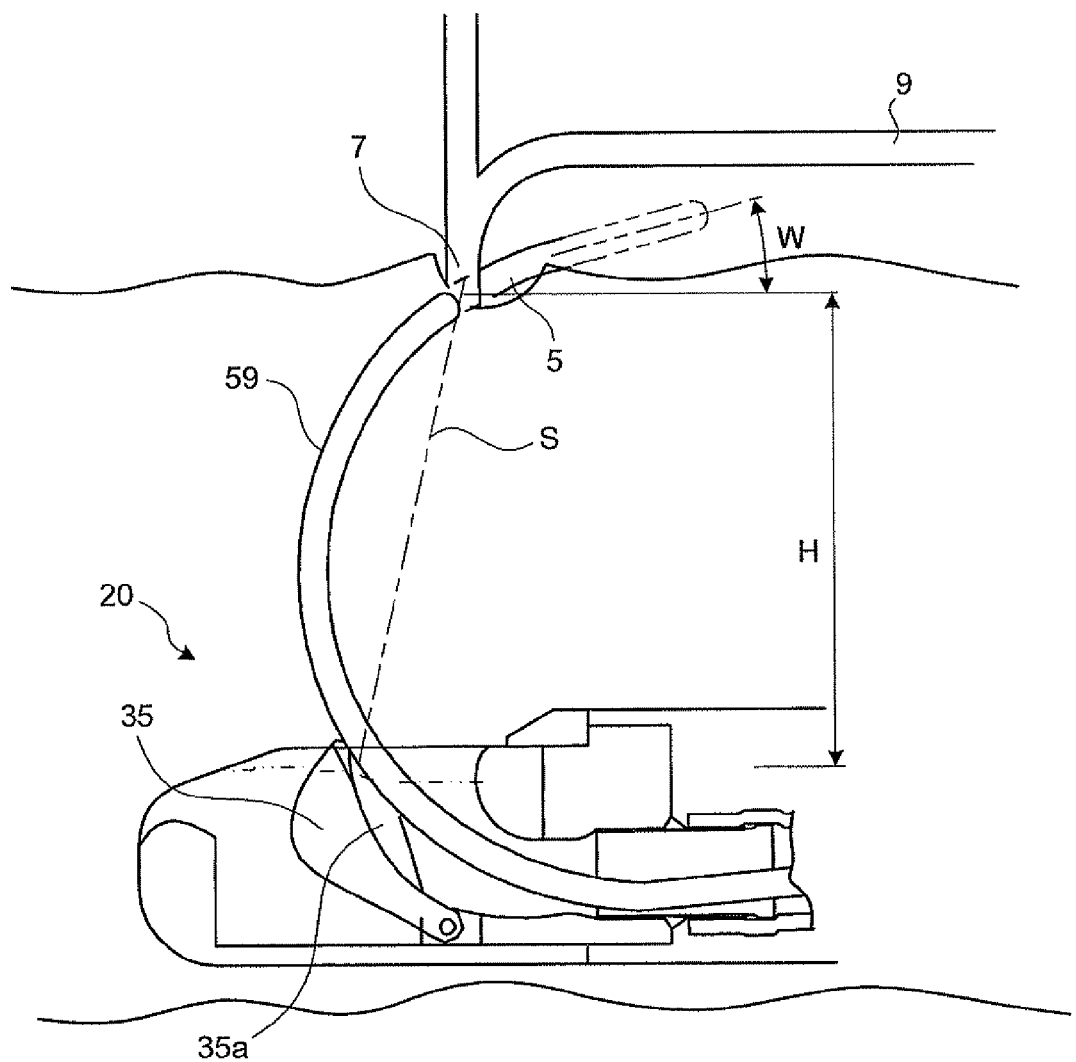
FIG. 19 is a view partially showing a section of the distal end portion shown in FIG. 18 for explaining the operation of the contrast tube during the insertion into a bile duct.
Figure 20:
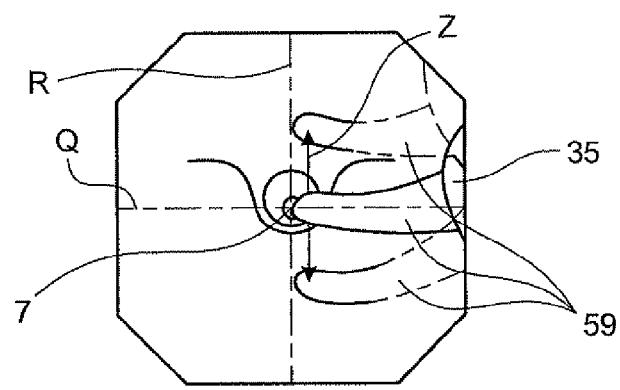
FIG. 20 is a view showing an endoscopic image with the state shown in FIG. 19.

FIGS. 18 to 20 show a second modification. FIG. 18 shows that bending tendency is given to a contrast tube 59, made of Teflon (registered trademark), for example, by advancing or retreating the contrast tube 59 back and forth several times with the treatment instrument raising stand 35 raised. FIG. 19 is a view for explaining the operation upon inserting the contrast tube 59 into a bile duct 9. In FIG. 19, the contrast tube 59 to which the bending tendency is given by the operation in FIG. 18 is lowered so as to coincide the tip of the contrast tube 59 with the papillary opening portion 7 that is apart by the distance H (about 20 mm). When the contrast tube 59 is pushed into the papillary opening portion 7 with this state, the distal end of the contrast tube 59 moves in the direction indicated by the two-dot-chain line. Supposing that its projecting angle is W, the bending tendency can be given by the simple operation shown in FIG. 18 so as to facilitate a selective contrast to the side of the bile duct 9, i.e., so as to establish 0°≦W≦60°.

FIG. 20 is an image of the endoscope in FIG. 19. The two-dot-chain line in FIG. 20 indicates the position of the contrast tube 59 when the treatment instrument raising stand 35 is moved up and down. In FIG. 20, the locus Z of the distal end of the contrast tube 59 moves on the line indicated by an arrow at the position slightly apart from the center line R that divides the image equally in the vertical direction and side-to-side direction. Specifically, the treatment instrument raising stand 35 or the guide channel 35a is held or formed with a predetermined angle such that the distal end of the contrast tube 59 does not go over the center line R at a position apart by the distance H. As a result, even if the contrast tube 59 whose distal end is very thicker than the guide wire 5 is used, it is prevented that the distal end of the contrast tube 59 covers the papillary opening portion 7 to make it difficult to observe the papillary opening portion 7.

Second Embodiment

Figure 21:
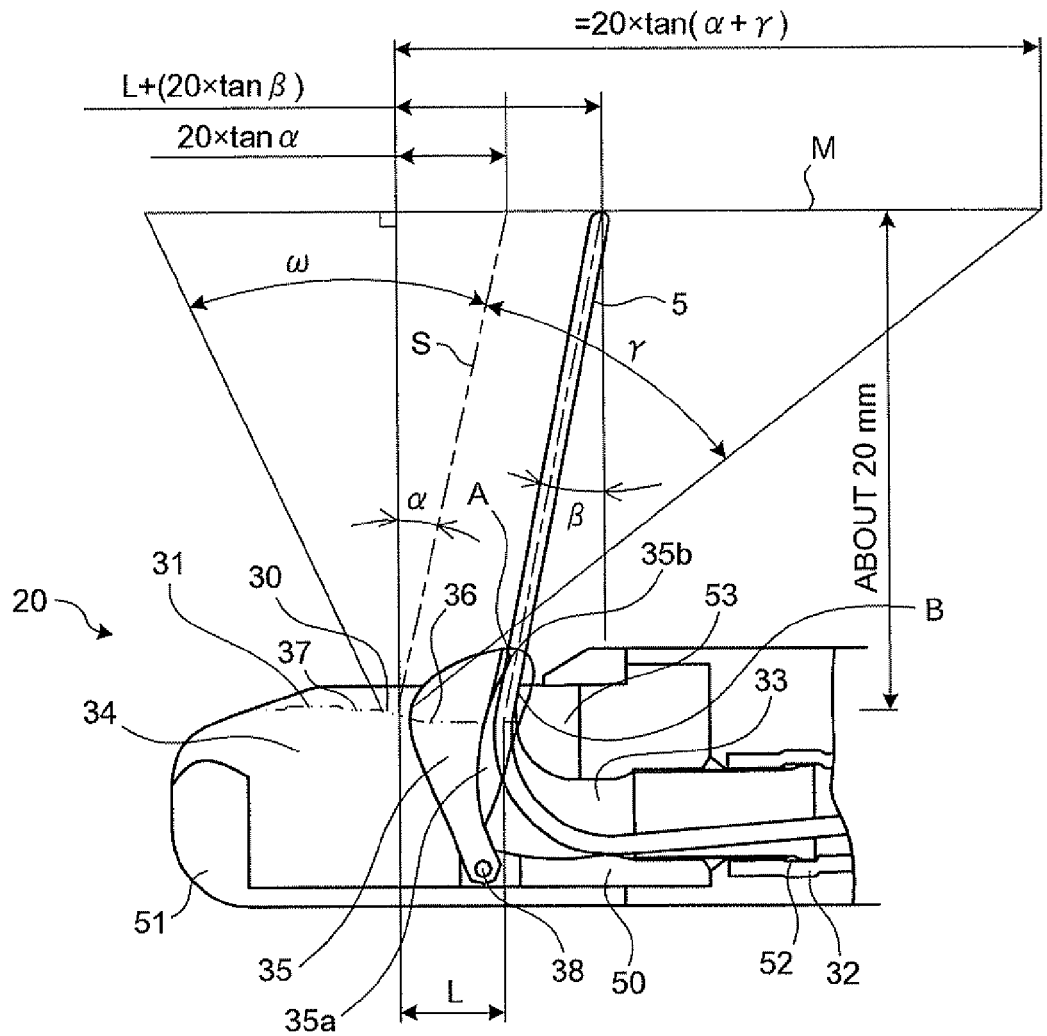
FIG. 21 is a view partially showing a section of the distal end portion shown in FIG. 1 when a guide wire according to a second embodiment is brought into its fixed state by a treatment instrument raising stand maximally raising.
Figure 22:
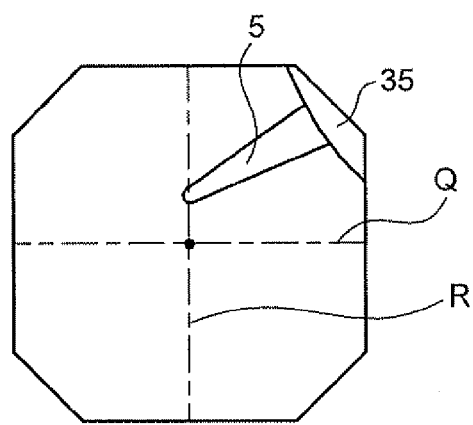
FIG. 22 is a view showing an endoscopic image with the state shown in FIG. 21.

FIG. 21 is a view showing a part of the section of the distal end portion shown in FIG. 1 when the guide wire according to a second embodiment is fixed by maximally raising the treatment instrument raising stand. FIG. 22 is a view showing an image of the endoscope in the state shown in FIG. 21. The second embodiment defines the position of the distal end portion of the guide wire 5, which is in its fixed state, from the relationship of the tilt angle α of the central axis S of the field of view of the observation window 30, the tilt angle β of the guide wire 5, and the angle of view γ at the upper section from the center of the field of view when the guide wire 5 is maximally raised by the treatment instrument raising stand 35.

In these figures, the tilt angle α is the tilt angle of the central axis S of the field of view as described above, i.e., it is an angle made by the direction perpendicular to the axial direction of the distal end portion 20 and the central axis S of the field of view. The angle of view γ is the range of the field of view, shown in FIG. 22, at the upper section (at the proximal end side of the distal end portion 20) from the center line Q that divides the image of the endoscope equally in the vertical direction. The angle of view ω is the range of the field of view at the lower section from the center line Q that divides the image of the endoscope equally in the vertical direction. In this embodiment, the position of the distal end portion of the guide wire 5, which is in its fixed state, is set so as to satisfy the relational expression described below.

$$20 \tan \alpha \leq L + 20 \tan \beta < 20 \tan(\alpha+\gamma)$$

In the expression, L is a horizontal distance in the axial direction between the proximal end portion of the guide wire that is maximally raised and the center of the field of view on the observation window.

A series of operations from the insertion of the guide wire 5 into the bile duct 9 to the replacement of the treatment instrument by using the endoscope 1 according to the present embodiment is the same as those shown in FIGS. 10 to 15. Like FIGS. 10 and 11, the position of the distal end portion (distal point) of the fixed guide wire 5 reaches the proximal end side (at the upper side in FIG. 21) from the central axis S of the field of view at a distance of about 20 mm apart from the observation window 30 of the distal end portion 20 of the endoscope 1 inserted into the duodenum 6. The papillary opening portion 7 and the neighboring papilla 8 are well observed at the basic position of the central axis S of the field of view where the papillary opening portion 7 is caught. Then, like FIGS. 12 and 13, the treatment instrument raising stand 35 is slightly lowered. With this operation, the distal end portion of the guide wire 5 is changed to the position of the papillary opening portion 7, and then, the guide wire 5 is inserted into the bile duct 9 from the papillary opening portion 7. This operation can also be performed with the basic position maintained at all times. Next, like FIGS. 14 and 15, the guide wire 5 is inserted to an appropriate depth of the bile duct 9. Then, the treatment instrument raising stand 35 is maximally raised to fix the guide wire 5. With this operation, the guide wire 5 can also easily be fixed with the basic position maintained.

As described above, in this embodiment, when the guide wire 5 is maximally raised on the treatment instrument raising stand 35, the treatment instrument raising stand 35 is maximally raised so as to satisfy $20 \tan \alpha \leq L + 20 \tan \beta < 20 \tan(\alpha+\gamma)$. By virtue of this, in this embodiment, the distal point of the guide wire 5 can be positioned in the area in the vicinity of the center line Q, which divides the screen of the endoscopic image equally in the vertical direction, or at the upper section (at the base side of the distal end portion 20) from the center line Q as shown in FIG. 22 like the first embodiment. According to this embodiment, the distal point of the guide wire 5 is positioned as described above, whereby a treatment instrument can simply and more safely be replaced via a guide wire 5, while always observing the papillary opening portion 7 as a portion to be treated from the front (in a basic position where the portion to be treated is positioned at the center of the field of view).

Third Embodiment

Figure 23:
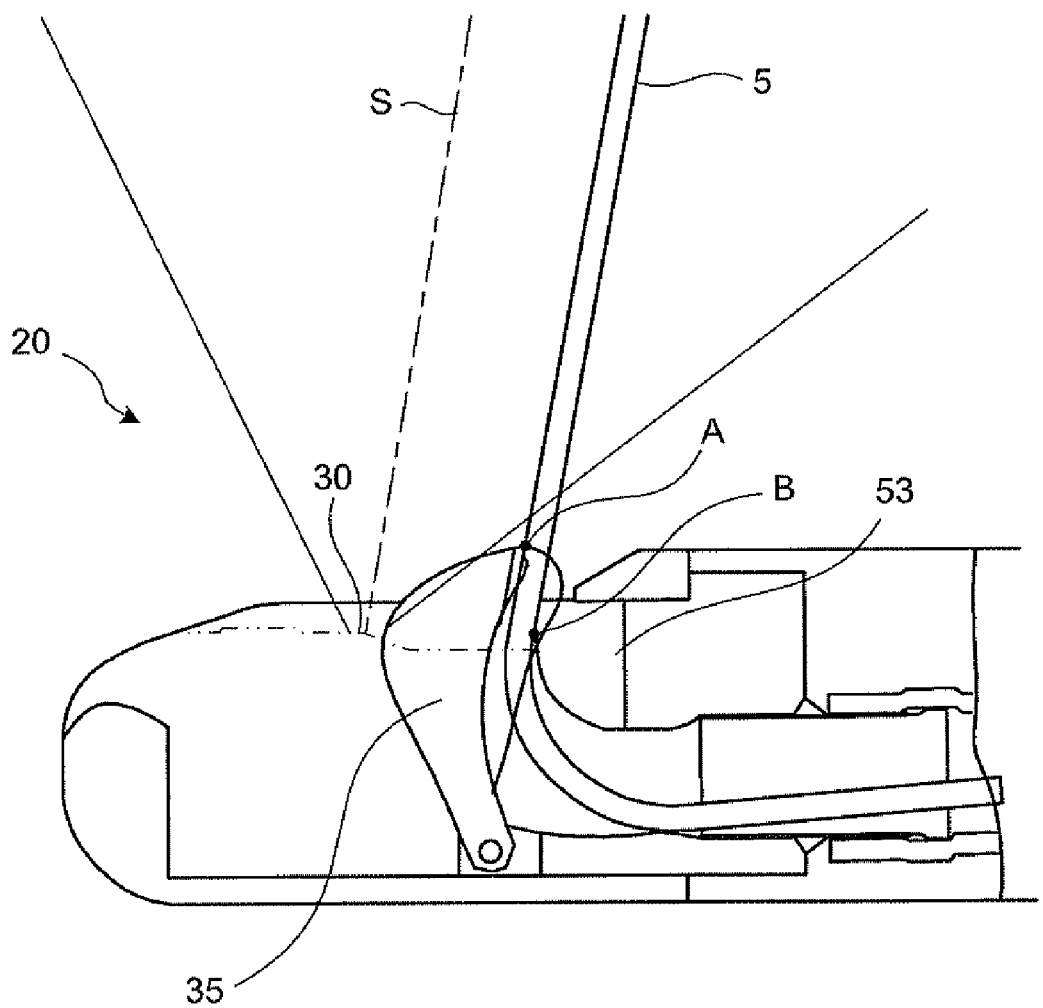
FIG. 23 is a view partially showing a section of the distal end portion shown in FIG. 1 according to a third embodiment.

FIG. 23 is a view showing a part of the section of the distal end portion 20 shown in FIG. 1 according to a third embodiment. This embodiment is same as the second embodiment in that the position of the distal end portion of the guide wire 5, which is in its fixed state, is set so as to satisfy $20 \tan \alpha \leq L + 20 \tan \beta < 20 \tan(\alpha+\gamma)$.

Specifically, in this embodiment, the maximally raising angle of the guide wire 5 is made parallel to the central axis S of the field of view, and the guide wire 5 is inserted into the bile duct 9, as shown in FIG. 23. Thereafter, the raising angle of the treatment instrument raising stand 35 is made maximum as shown in FIG. 14 so as to fix the guide wire 5.

According to this embodiment too, the effect same as that of the second embodiment can be obtained. In this case, the position of the observation window 30 and the raising cardinal point (the point A and the point B) can be shortened compared to the case of the second embodiment.

Fourth Embodiment

Figure 24:
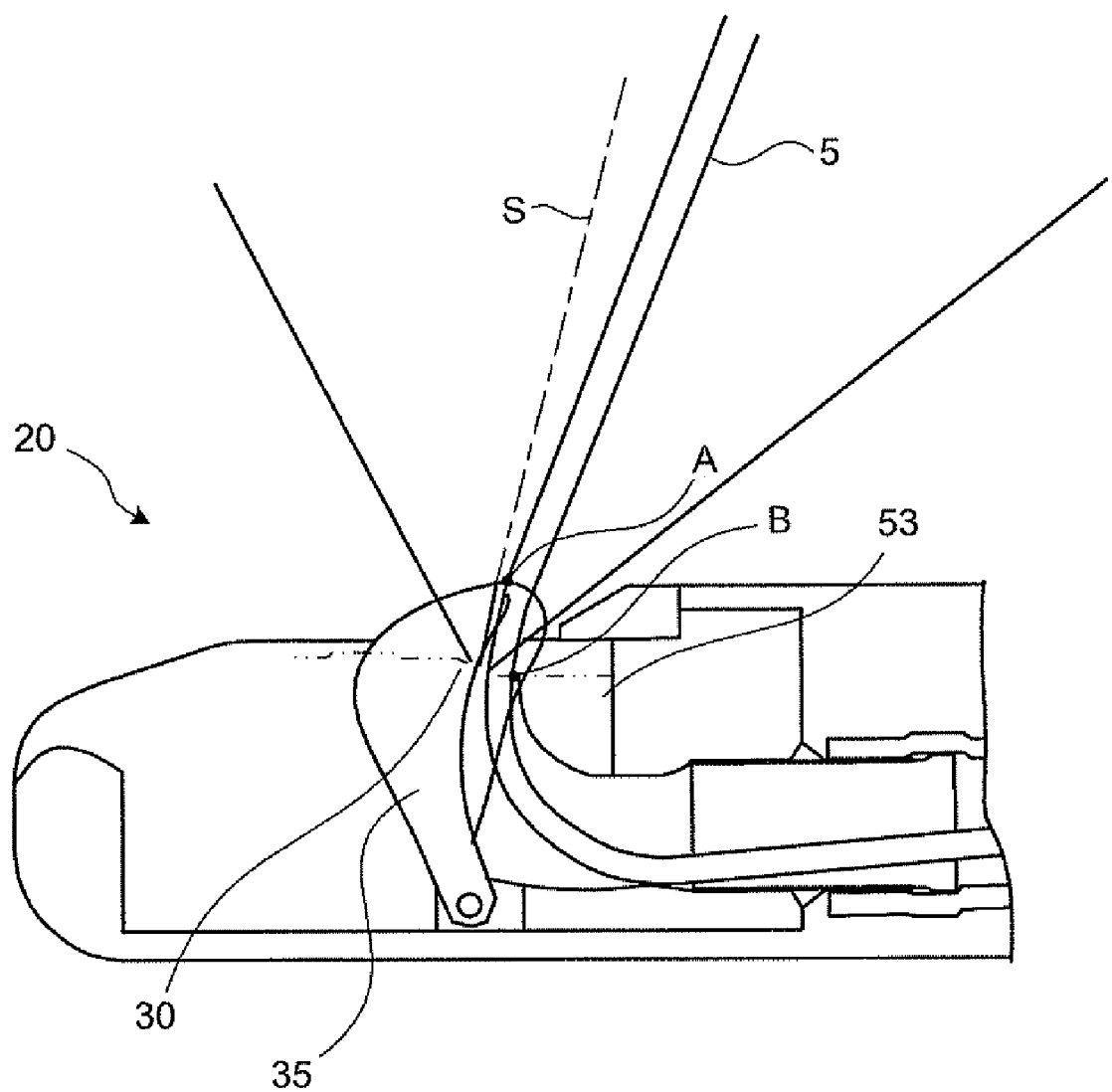
FIG. 24 is a view partially showing a section of the distal end portion shown in FIG. 1 according to a fourth embodiment.

FIG. 24 is a view showing a part of the section of the distal end portion 20 shown in FIG. 1 according to a fourth embodiment. In this embodiment, the maximum raising angle of the guide wire 5 is made greater than the tilt angle of the central axis S of the field of view. Then, after the guide wire 5 is inserted into the bile duct 9, the raising angle of the treatment instrument raising stand 35 is made maximum so as to fix the guide wire 5 as shown in FIG. 14.

According to this embodiment too, the effect same as that of the second embodiment can be obtained. In this case, the position of the observation window 30 and the raising cardinal point (the point A and the point B) can be shortened compared to the case of the second embodiment.

Fifth Embodiment

Figure 25:
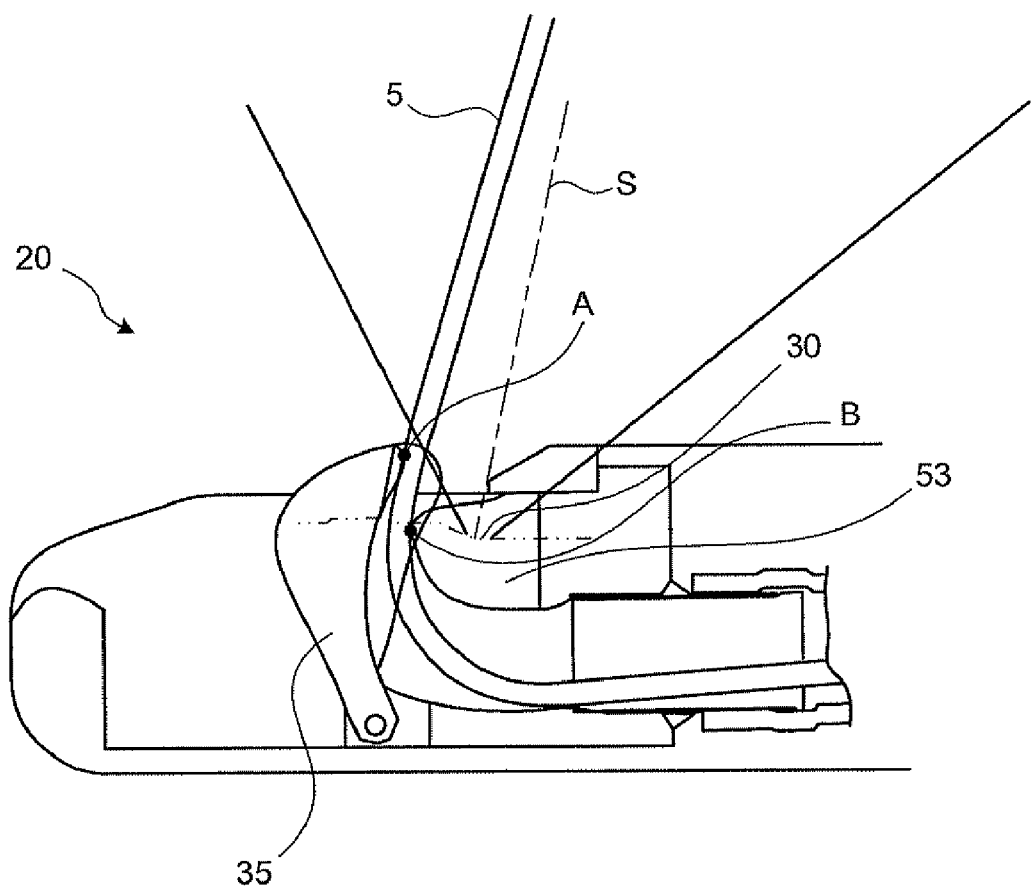
FIG. 25 is a view partially showing a section of the distal end portion shown in FIG. 1 according to a fifth embodiment.
Figure 26:
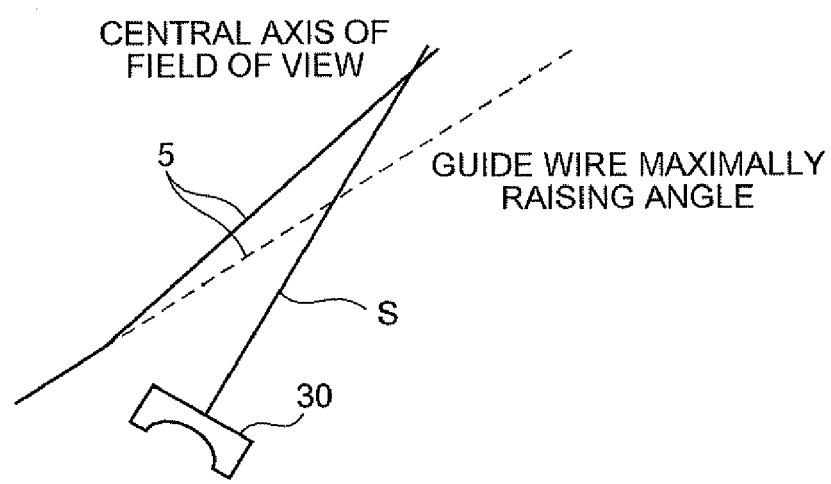
FIG. 26 is a schematic view showing a relationship between the guide wire and a central axis of the field of view when the guide wire shown in FIG. 25 is fixed.

FIG. 25 is a view showing a part of the section of the distal end portion 20 shown in FIG. 1 according to a fifth embodiment. In this embodiment, the observation window 30 is mounted not at the distal end portion 20 but at the insulating block 53, and the maximum raising angle of the guide wire 5 upon inserting the guide wire 5 into the bile duct 9 is made greater than the tilt angle of the central axis S of the field of view. After the guide wire 5 is inserted into the bile duct 9, the raising angle of the treatment instrument raising stand 35 is made maximum so as to fix the guide wire 5 as shown in FIG. 26.

According to this embodiment too, the effect same as that of the second embodiment can be obtained. In this case, the raising cardinal point (the point A and the point B) can be positioned closer to the side of the distal end portion 20 than to the observation window 30.

Figure 27:
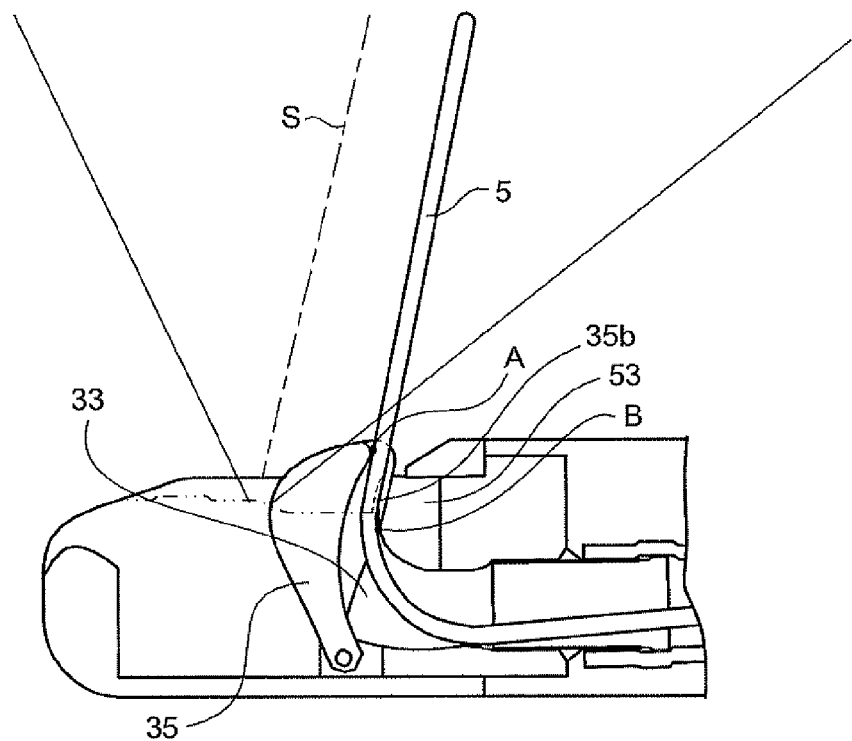
FIG. 27 is a view partially showing a section of the distal end portion shown in FIG. 1 when a guide wire according to a first modification of the second embodiment is brought into its fixed state by a treatment instrument raising stand maximally raising.

FIG. 27 is a view showing a part of the section of the distal end portion shown in FIG. 1 when the guide wire is fixed by the maximum raise of the treatment instrument raising stand according to a first modification of the second embodiment. This modification is different in that the guide wire housing channel 35b is formed not at the treatment instrument raising stand 35 but at the side of the treatment instrument lead-out port 33.

Figure 28:
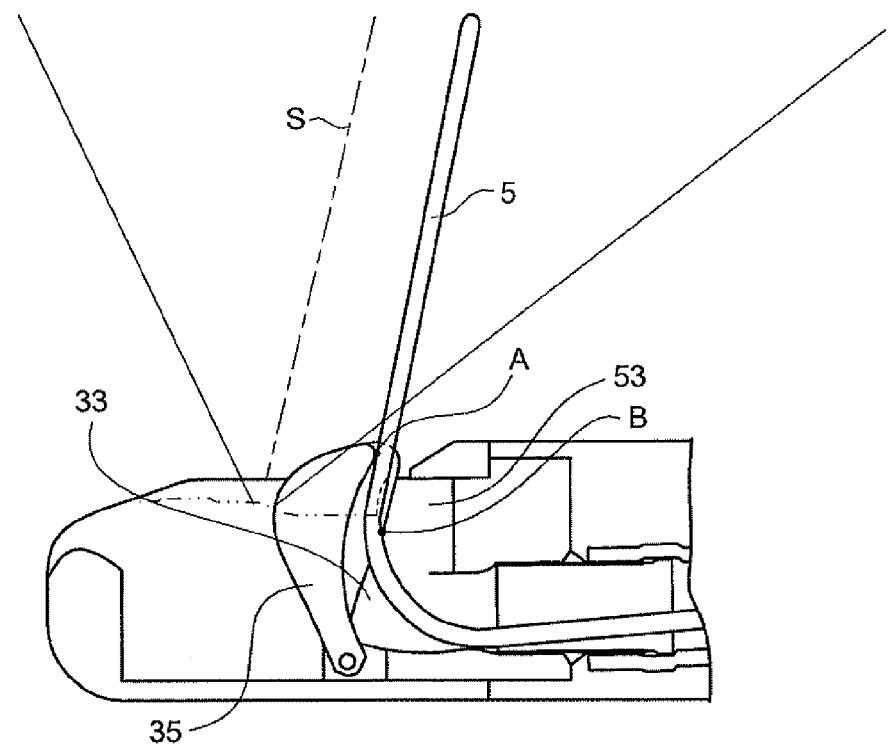
FIG. 28 is a view partially showing a section of the distal end portion shown in FIG. 1 when a guide wire according to a second modification of the second embodiment is brought into its fixed state by a treatment instrument raising stand maximally raising.

FIG. 28 is a view showing a part of the section of the distal end portion shown in FIG. 1 when the guide wire is fixed by the maximum raise of the treatment instrument raising stand according to a second modification of the second embodiment. In this modification, the guide wire housing channel 35b is not formed, and the distance between the point A and the point B is shortened by that much to secure the fixing strength equal to that in the second embodiment.

According to the first and second modifications, a treatment instrument can simply and more safely be replaced via a guide wire, while always observing a portion to be treated (papillary opening portion 7) from the front (in a basic position where the portion to be treated is positioned at the center of the field of view).

Sixth Embodiment

Figure 29:
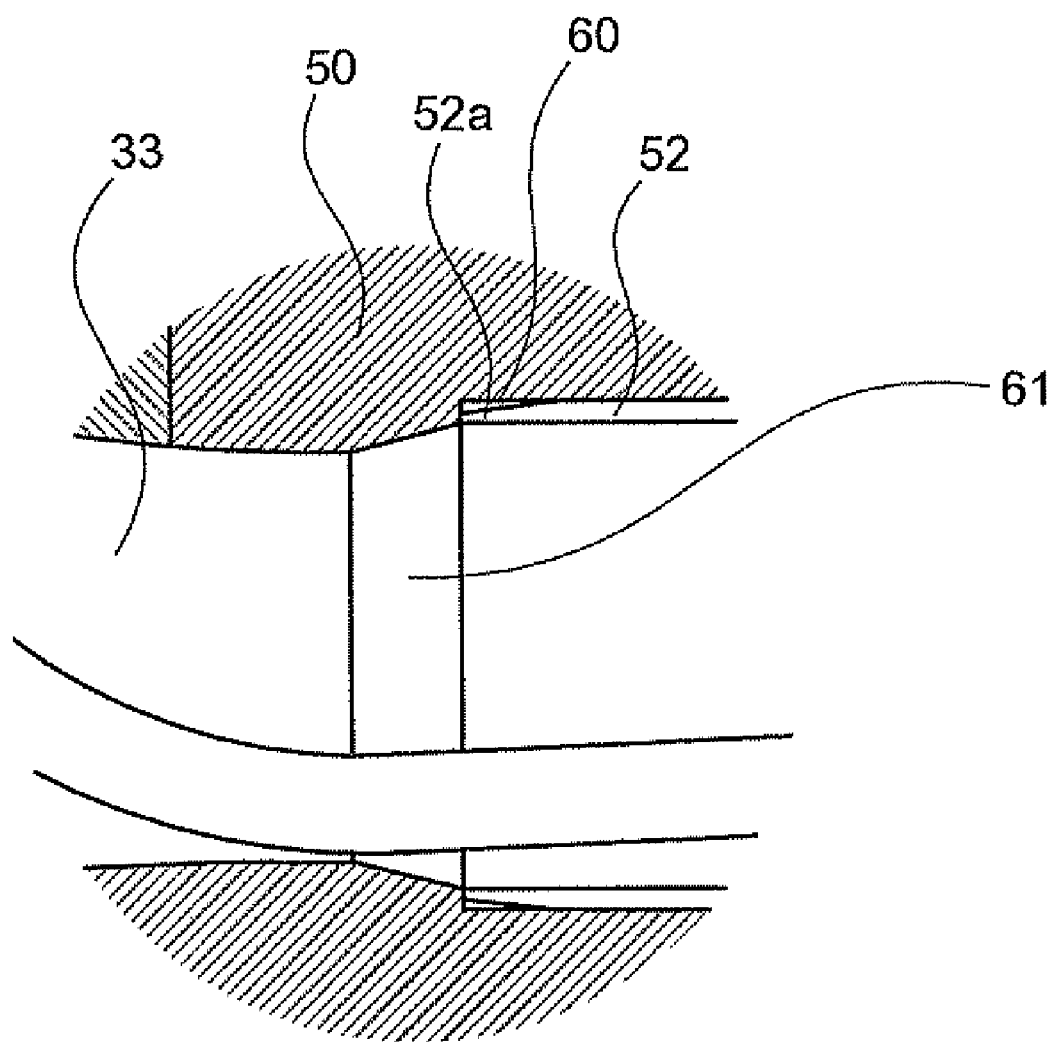
FIG. 29 is a partially enlarged view of a treatment instrument lead-out port at the distal end portion according to a sixth embodiment.

FIG. 29 is a partially enlarged view of the treatment instrument lead-out port at the distal end portion according to a sixth embodiment. In this embodiment, a taper 52a is formed at the outer periphery of the joint member 52 at the side of the distal end portion. A puddle of an adhesive 60 is produced between the distal end portion composing unit 50 and the joint member 52 due to this taper 52a. Therefore, according to this embodiment, the distal end portion composing unit 50 and the joint member 52 can firmly be bonded and fixed up to the end face without forming a gap between the distal end portion composing unit 50 and the joint member 52.

A channel internal diameter decreasing portion 61 whose internal diameter gently decreases is formed at the front side (distal end side) of the joint member 52, whereby unstable movement of the treatment instrument, which is inserted into the channel and has a small diameter, can be reduced. Further, this configuration provides an advantage that the suction performance is hardly deteriorated since the rearward (in the direction toward the base) from the joint member 52 has a large internal diameter.

Seventh Embodiment

Figure 30:
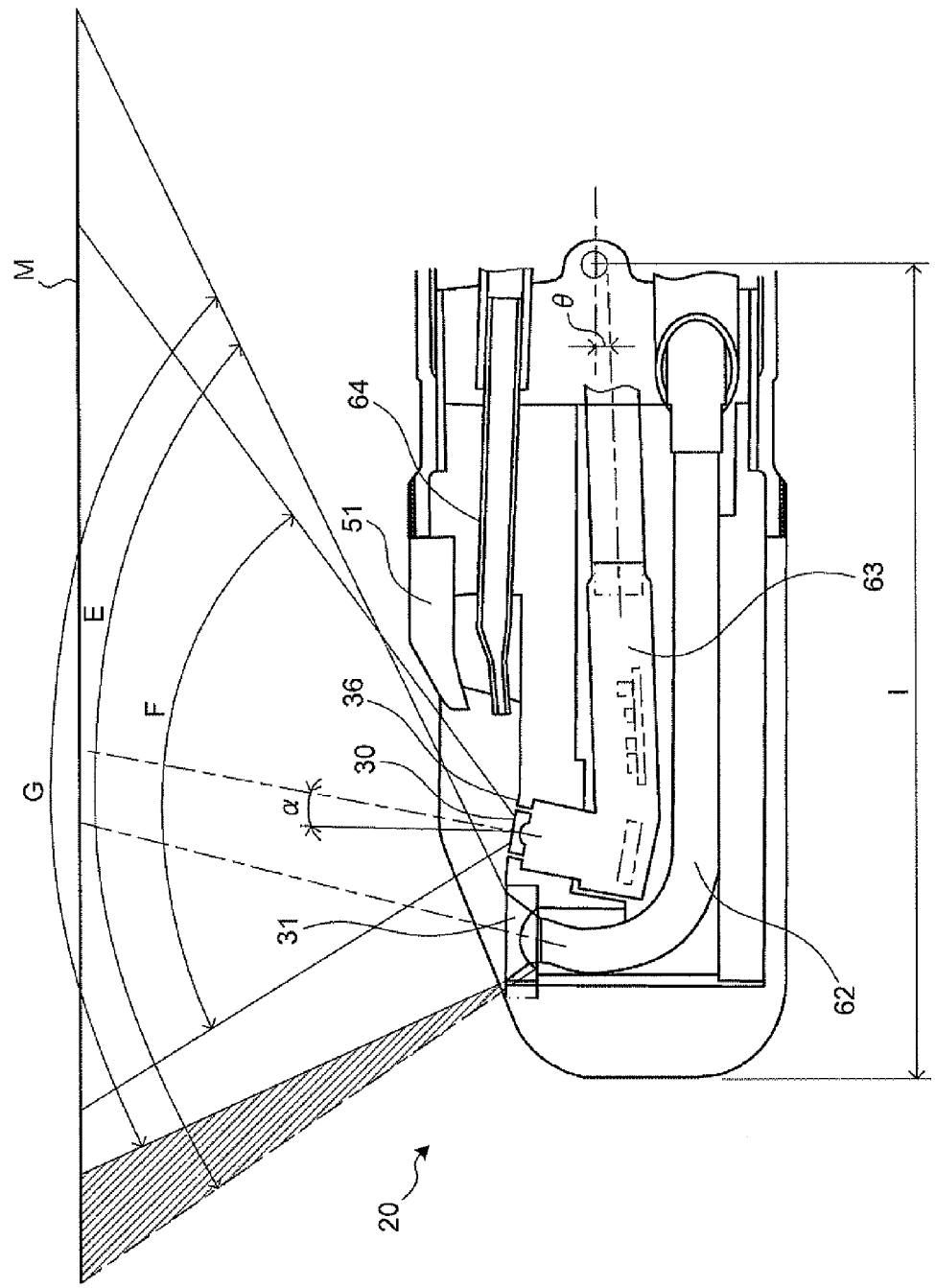
FIG. 30 is a sectional view of an observation window and an illumination window shown in FIG. 1 in the axial direction according to a seventh embodiment.

FIG. 30 is a sectional view showing a section of the observation window 30 and the illumination window 31 shown in FIG. 1 in the axial direction according to a seventh embodiment. The feature of this embodiment is that the distal end of the illumination window 31 is partially cut. The symbol F indicates the observation range from the observation window 30, and symbols E and G indicate the illumination range from the illumination window 31. If the illumination window 31 before being cut is used, the light from a light guide fiber 62 illuminates the range of E. However, the hatched portion in the range of E is outside the observation range F, which means that unnecessary range is illuminated.

In view of this, the distal end portion of the illumination window 31 is cut in this embodiment so as to obtain the illumination range of G. By cutting the illumination window 31 as described above, the illumination window 31, light guide fiber 62, observation window 30, imaging unit 63, and the like can be arranged at the distal end portion side of the endoscope as a whole. Consequently, the length l of the distal end portion composing unit can be shortened in this embodiment. Accordingly, the length of the rigid part of the distal end portion is shortened, whereby handleability is enhanced, and insertability into a subject to be treated and operability are enhanced.

The imaging unit 63 is mounted as tilted with an angle of $\theta$ with respect to the axial direction of the distal end portion 20. If the tilt angle $\theta$ is changed, a device having a different rearward oblique visual angle $\alpha$ can easily be formed by the same imaging unit 63. Therefore, the length of the rigid part of the imaging unit is shortened, which reduces the length of the rigid part of the distal end portion. Even when the distal end cover 51 is seen in the field of view due to the variation in the optical system, the distal end cover 51 is prevented to be in the observation range F only by slightly changing the oblique visual angle $\alpha$ according to this embodiment. Therefore, a countermeasure can easily be taken.

The observation window 30 is mounted to the inclined surface 36. Therefore, the light emitted from the illumination window 31 in the horizontal direction is not incident on the observation window 30, whereby flare is difficult to occur on the screen. Further, since the inclined surface 36 does not have a step but has a gentle slope, air and water supplied from the nozzle 64 naturally flows, and excellent draining property can be obtained.

INDUSTRIAL APPLICABILITY

As described above, the endoscope according to the present invention is useful for a device that is inserted into a body cavity of a subject so as to observe the biological tissue in the body cavity and to perform an incision or coagulation of the biological tissue. Particularly, the endoscope according to the present invention is adaptable to simply and more safely replace a treatment instrument via a guide wire, while always observing a portion to be treated from the front (in a basic position where the portion to be treated is positioned at the center of the field of view).

The invention claimed is:
1. An endoscope comprising:
    an insertion unit that is inserted into a body cavity;
    an observation optical system that is provided with an observation window formed at a distal end portion of the insertion unit and has a central axis of a field of view in a predetermined direction;
    a treatment instrument insertion channel that is provided in the insertion unit and is open to the distal end portion of the insertion unit; and
    a treatment instrument raising stand that is capable of guiding a guide wire, which is inserted from a proximal end side of the treatment instrument insertion channel and led out into the body cavity from the distal end portion of the insertion unit in a substantially vertical direction of an endoscopic image taken by the observation optical system,
    wherein:
        when the guide wire is maximally raised on the treatment instrument raising stand and a distal end of the guide wire is positioned at a position apart from the observation window by about 20 mm, a tilt angle of the central axis of the field of view of the observation window and a tilt angle of the guide wire at when the treatment instrument raising stand is maximally raised are set so as to position the distal end of the guide wire near a central line, which divides a screen of the endoscopic image equally in the vertical direction, or positioned at an area above the central line, and
        when the guide wire is maximally raised on the treatment instrument raising stand and the distal end of the guide wire is positioned at the position apart from the observation window by about 20 mm, the distal end of the guide wire is positioned near the central line or posi- tioned at the area above the central line, by positioning the guide wire to have a tilt angle equal to or smaller than the tilt angle of the central axis of the field of view of the observation window.

2. The endoscope according to claim 1 further comprising a guide wire fixing mechanism configured to firmly fix the guide wire that is maximally raised by the treatment instrument raising stand.

3. The endoscope according to claim 1, wherein a point at which the guide wire that is maximally raised on the treatment instrument raising stand intersects a plane located at a position apart from the observation window by about 20 mm is positioned closer to a proximal end side of the insertion unit than to a position at which the central axis of the field of view of the observation window intersects the plane.

4. An endoscope comprising:
an insertion unit that is inserted into a body cavity;
an observation optical system that is provided with an observation window formed at a distal end portion of the insertion unit and has a central axis of a field of view in a predetermined direction;
a treatment instrument insertion channel that is provided in the insertion unit and is open to the distal end portion of the insertion unit; and
a treatment instrument raising stand that is capable of guiding a guide wire, which is inserted from a proximal end side of the treatment instrument insertion channel and led out into the body cavity from the distal end portion of the insertion unit in a substantially vertical direction of an endoscopic image taken by the observation optical system, wherein:
when the guide wire is maximally raised on the treatment instrument raising stand and a distal end of the guide wire is positioned at a position apart from the observation window by about 20 mm, a tilt angle of the central axis of the field of view of the observation window and a tilt angle of the guide wire at when the treatment instrument raising stand is maximally raised are set so as to position the distal end of the guide wire near a central line, which divides a screen of the endoscopic image equally in the vertical direction, or positioned at an area above the central line, and
when the guide wire is maximally raised on the treatment instrument raising stand and the distal end of the guide wire is positioned at the position apart from the observation window by about 20 mm, the distal end of the guide wire is positioned near the central line or positioned at the area above the central line, so that a relationship between a tilt angle $\alpha$ of the central axis of the field of view of the observation window, a tilt angle $\beta$ of the guide wire, and an angle of view $\gamma$ above the center of the field of view satisfies $$20 \tan \alpha \leq L + 20 \tan \beta < 20 \tan(\alpha+\gamma),$$

wherein L is a horizontal distance in an axial direction between a proximal end portion of the guide wire which is maximally raised and the center of the field of view on the observation window.

5. The endoscope according to claim 4, wherein a point at which the guide wire that is maximally raised on the treatment instrument raising stand intersects a plane located at a position apart from the observation window by about 20 mm is positioned closer to a proximal end side of the insertion unit than to a position at which the central axis of the field of view of the observation window intersects the plane.

6. The endoscope according to claim 4, further comprising a guide wire fixing mechanism configured to firmly fix the guide wire that is maximally raised by the treatment instrument raising stand.

* * * * *